US008541025B2

(12) United States Patent
Dokou et al.

(10) Patent No.: US 8,541,025 B2
(45) Date of Patent: Sep. 24, 2013

(54) CO-CRYSTALS AND PHARMACEUTICAL FORMULATIONS COMPRISING THE SAME

(75) Inventors: Eleni Dokou, Cambridge, MA (US); Rahela Gasparac, Watertown, MA (US); Dragutin Knezic, Watertown, MA (US); Billie J. Kline, Kingston, MA (US); Valdas Jurkauskas, Cambridge, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 133 days.

(21) Appl. No.: 13/034,039

(22) Filed: Feb. 24, 2011

(65) Prior Publication Data

US 2011/0236478 A1    Sep. 29, 2011

Related U.S. Application Data

(63) Continuation of application No. PCT/US2009/055384, filed on Aug. 28, 2009.

(60) Provisional application No. 61/093,972, filed on Sep. 3, 2008, provisional application No. 61/093,942, filed on Sep. 3, 2008.

(51) Int. Cl.
*A61K 9/20* (2006.01)
*A61K 31/4965* (2006.01)

(52) U.S. Cl.
USPC ..................................... 424/465; 514/255.05

(58) Field of Classification Search
None
See application file for complete search history.

(56) References Cited

U.S. PATENT DOCUMENTS

| | | | |
|---|---|---|---|
| 3,133,081 A | 5/1964 | Lafferty et al. |
| 3,755,322 A | 8/1973 | Winter et al. |
| 3,930,970 A | 1/1976 | Barton |
| 3,998,951 A | 12/1976 | Harnish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 6,558,657 B1 | 5/2003 | Mandeville, III et al. |
| 6,562,971 B2 | 5/2003 | Frauenkron et al. |
| 6,569,499 B2 | 5/2003 | Grammatica et al. |
| 6,579,983 B1 | 6/2003 | Batchelor et al. |
| 6,589,958 B1 | 7/2003 | Frietz |
| 6,593,326 B1 | 7/2003 | Bradbury et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,641,579 B1 | 11/2003 | Bernardi et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,716,851 B2 | 4/2004 | Cai et al. |
| 6,727,251 B2 | 4/2004 | Bebbington et al. |
| 6,743,791 B2 | 6/2004 | Cao et al. |
| 6,825,190 B2 | 11/2004 | Moon et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,884,804 B2 | 4/2005 | Choon-Moon |
| 6,919,338 B2 | 7/2005 | Mortlock et al. |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,739 B2 | 10/2006 | Bebbington et al. |
| 7,179,826 B2 | 2/2007 | Bebbington et al. |
| 7,253,187 B2 | 8/2007 | Cao et al. |
| 7,304,061 B2 | 12/2007 | Hale et al. |
| 2002/0052386 A1 | 5/2002 | Armistead et al. |

(Continued)

FOREIGN PATENT DOCUMENTS

| | | |
|---|---|---|
| EP | 00198811 | 12/1980 |
| EP | 0136976 | 4/1985 |

(Continued)

OTHER PUBLICATIONS

Almarsson et al. (Chem. Commun., 2004, 1889-1896) Crystal engineering of the composition of pharmaceutical phases . . . .*
Shah et al. (Drug Development and Industrial Pharmacy, 12, 1329-1346, 1986) Evaluation of two new tablet lubricants . . . .*
Park et al. (Journal of Applied Polymer Science 105, 2824-2829) Separation of hydroxybenzoic acid isomers . . . .*
Park et al. (Journal of Applied Polymer Science 105, 2824-2829) Separation of hydroxybenzoic acid isomers . . . , 2007.*
Hamdane, M. et al., "Pin 1—A Therapeutic Target in Alzheimer Neurodegeneration," J. Mol. Neurosci., 19(3): 275:87 (2002).
Haq. S. et al., "Glycogen Synthase Kinase-3β Is a Negative Regulator of Cardiomyocyte Hypertrophy", J. Cell Biol., 151(1), 177-129 (2000).
Hardt, S.E., et al., "Glycogen Synthase Kinase-3β—A Novel Regulator of Cardiac Hypertrophy and Development," Circulation Research, 90: 1055-1063 (2002).
Harrington, E.A. et al., "VX-680, a potent and selective small-molecule inhibitor of the Aurora kinases, suppresses tumor growth in vivo," Nat. Med., 10(3): 262-267 (2004).
Haworth, R.D. et al. "Synthetic antimalarials. Part XXVII. Some derivatives of phthalazine, quinoxaline, and isoquinoline", J. Chem. Soc., 777-782 (1948).

(Continued)

*Primary Examiner* — David J Blanchard
*Assistant Examiner* — Tigabu Kassa
(74) *Attorney, Agent, or Firm* — Min Lin

(57) ABSTRACT

An immediate release formulation of an active ingredient.

28 Claims, 3 Drawing Sheets

(56) References Cited

U.S. PATENT DOCUMENTS

| | | | |
|---|---|---|---|
| 2002/0065270 | A1 | 5/2002 | Moriarty et al. |
| 2003/0064982 | A1 | 4/2003 | Davies et al. |
| 2003/0069248 | A1 | 4/2003 | Chakravarty et al. |
| 2003/0096813 | A1 | 5/2003 | Cao et al. |
| 2003/0105090 | A1 | 6/2003 | Bebbington et al. |
| 2003/0199526 | A1 | 10/2003 | Choquette et al. |
| 2003/0207873 | A1 | 11/2003 | Harrington et al. |
| 2004/0009981 | A1 | 1/2004 | Bebbington et al. |
| 2004/0097531 | A1 | 5/2004 | Ledeboer et al. |
| 2004/0157893 | A1 | 8/2004 | Bebbington et al. |
| 2004/0167141 | A1 | 8/2004 | Bebbington et al. |
| 2004/0214814 | A1 | 10/2004 | Bebbington et al. |
| 2005/0038023 | A1 | 2/2005 | Bebbington et al. |
| 2005/0234059 | A1 | 10/2005 | Hale et al. |
| 2006/0270660 | A1 | 11/2006 | Charrier et al. |
| 2007/0059356 | A1* | 3/2007 | Almarsson et al. ............ 424/464 |

FOREIGN PATENT DOCUMENTS

| | | | |
|---|---|---|---|
| EP | 0302312 | | 2/1989 |
| GB | 2052487 | | 1/1981 |
| JP | 06065237 | | 3/1994 |
| JP | 10130150 | | 5/1998 |
| JP | 2000026421 | | 1/2000 |
| WO | 9322681 | | 11/1993 |
| WO | 9509851 | | 4/1995 |
| WO | 9515758 | | 6/1995 |
| WO | 9614843 | | 5/1996 |
| WO | 9709325 | | 3/1997 |
| WO | 9719065 | | 5/1997 |
| WO | 9802434 | | 1/1998 |
| WO | 9811095 | | 3/1998 |
| WO | 9814450 | | 4/1998 |
| WO | 9816502 | | 4/1998 |
| WO | 9838171 | | 9/1998 |
| WO | 9918781 | | 4/1999 |
| WO | 9941253 | | 8/1999 |
| WO | 9947154 | | 9/1999 |
| WO | 9962518 | | 12/1999 |
| WO | 9965897 | | 12/1999 |
| WO | 0012497 | | 3/2000 |
| WO | 0021955 | | 4/2000 |
| WO | 0038675 | | 7/2000 |
| WO | 0039101 | | 7/2000 |
| WO | 0042029 | | 7/2000 |
| WO | 0059509 | | 10/2000 |
| WO | 0078757 | | 12/2000 |
| WO | 0112621 | | 2/2001 |
| WO | 0125220 | | 4/2001 |
| WO | 0144242 | | 5/2001 |
| WO | 0139777 | | 6/2001 |
| WO | 0140215 | | 6/2001 |
| WO | 0147879 | | 7/2001 |
| WO | 0147897 | | 7/2001 |
| WO | 0160816 | | 8/2001 |
| WO | 0164655 | | 9/2001 |
| WO | 0174768 | | 10/2001 |
| WO | 0179198 | | 10/2001 |
| WO | 0208244 | | 1/2002 |
| WO | 0218346 | | 3/2002 |
| WO | 0222601 | | 3/2002 |
| WO | 0222602 | | 3/2002 |
| WO | 0222603 | | 3/2002 |
| WO | 0222604 | | 3/2002 |
| WO | 0222605 | | 3/2002 |
| WO | 0222606 | | 3/2002 |
| WO | 0222607 | | 3/2002 |
| WO | 0222608 | | 3/2002 |
| WO | 0224667 | | 3/2002 |
| WO | 0247690 | | 6/2002 |
| WO | 0250065 | | 6/2002 |
| WO | 0250066 | | 6/2002 |
| WO | 02057259 | | 7/2002 |
| WO | 02059111 | | 8/2002 |
| WO | 02059112 | | 8/2002 |
| WO | 02062789 | | 8/2002 |
| WO | 02066461 | | 8/2002 |
| WO | 02068415 | | 9/2002 |
| WO | 02079197 | | 10/2002 |
| WO | 03026664 | | 4/2003 |
| WO | 200400833 | | 12/2003 |
| WO | 200413140 | | 2/2004 |
| WO | WO 2006007448 | * | 1/2006 |
| WO | 2007041358 | | 4/2007 |
| WO | 2007/098270 | A2 | 8/2007 |
| WO | WO 2007098270 | * | 8/2007 |
| WO | 2008/106151 | A2 | 9/2008 |
| WO | 2009/032198 | A1 | 3/2009 |

OTHER PUBLICATIONS

Heaney, F., et al., "Pyrimidine annelated heterocycles-synthesis and cycoaddition of the first pyrimido[1,4]diazepine N-oxides," J. Chem. Soc., Perkin Trans., 1:622-632 (2001).

Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Heutink, P., "Untangling tau-related dementia", Hum. Mol. Genet., 9(6): 979-986 (2000).

Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).

IUPAC Compendium of Chemical Terminology on a definition of "aliphatic compounds" found from http://www.chemsoc.org/chembytes/goldbook/index.htm (last visited on Nov. 18, 2007).

Ivashchenko A.V. et al., "Synthesis and Study of Heteroaromatic Ligands Containing a Pyrimidine Ring", Khim. Geterotsikl. Soedin., (12), 1673-7, (1980).

Jambhekar, S.S., "Biopharmaceutical Properties of Drug Substances" in Principles of Medicinal Chemistry, 4th ed., 12-24 (1995).

Jeffrey, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).

Katzung, Bertram G., Basic and Clinical Pharmacology, 7th Edition, 1998, pp. 881-884.

Kelarev, V.I. et al., "Synthesis of amino derivatives of 1,3,5-triazine containing 1,3-4-thiadiazole fragments," Izvestiya Vysshikh Uchebnkh Zavedenii, Khimiya I Khimicheskaya Tekhnologiya, 40(5):27-32 (1997).

Kim, L. et al., "GSK3, a master switch regulating cell-fate specification and tumorigenesis" Current Opinion in Genetics & Development, 10:508-514 (2000).

Kim, Y.Z. et al., "Synthesis and Antimicrobial Activity of Novel [)3-Aminopyrimidiniumyl)thio]methyl Cephalosporins", J. Med. Chem., 37(22); 3828-3833 (1994).

Kimura M. et al., "Cell Cycle-dependent Expression and Centrosome Localization of a Third Human Aurora/Ipl1-related Protein Kinase, AIK3", J. Biol. Chem., 274(11), 7334-7340 (1999).

Klein, P.S. et al., "A molecular mechanism for the effect of lithium on development", PNAS, 93:8455-8459 (1996).

Layzer, R.B., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylguinazolines Possessing Cyclic GMP Phosphodiesterase and Thromboxane Synthesis Inhibitory Activities," J. Med. Chem., 38 (18):3547-3557 (1995).

Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).

Lübbers, T. et al., "Design synthesis, and structure-activity relationship studies of ATP analogues as DNA gyrase inhibitors", Bioorg. Med. Chem. Lett., 10, 8, 821-826 (2000).

Lutz, M.L. et al., "Overexpression and Activation of the Tyrosine Kinase Src in Human Pancreatic Carcinoma", Biochem. Biophys. Res. 243, 503-508 (1998).

Lynch, S.A. et al., "Increased Expression of the src Proto-Oncogene in Hairy Cell Leukemia and a Subgroup of B-Cell Lymphomas", Leukemia, 7(9), 1416-1422 (1993).

Lyrer, P., Schweiz. "Neue Ansätze in der Akutbehandlung des zerebrovaskulüren Insultes." Med. Woohen Schr., 124 (45); 2005-2012 (1994).

Mani, S. et al., "Cyclin-dependent kinase: novel anticancer agents", Exp. Opin. Invest. Drugs, 8, 1849-1870 (2000).

Masaki, T. et al., "pp60c-src Activation in Hepatocellular Carcinoma of Humans and LEC Rats", Hapatology, 27, 1257 (1998).

Massillon, D. et al., "Identification of the glycogenic compound 5-iodotubercidin as a general protein kinase inhibitor", Biochem J., 299: 123-128 (1994).

Medwid, Jeffrey B. et al., "Preparation of triazolo 1, 5-cipyrimidines as potential antiasthma agents," J. Med. Chem., 33 (4): 1230-1241 (1990).

Molina, T.J. et al., "Profound block in thymocyte development in mice lacking p56Ick", Nature, 357, 161-164 (1992).

Moodie, S.A. et al., "Complexes of Ras-GTP with Raf-1 and Mitogen-Activated Protein Kinase", Science, 260 (5114), 1658-1661 (1993).

Moss, R.A. et al., "Conversion of 'Obstinate' Nitriles to Amidines by Garigipati's Reaction", Tetrahedron Lett., 36(48), 8761-8764 (1995).

Myers, M. R. et al., "The synthesis and SAR of new 4-(N-alkyl-N-phenyl)amino-6,7-dimethoxyquinazolines and 4-(N-alkyl-N-Phenyl)aminopyrazolo[3,4-d]pyrimidines, inhibitors of CSF-1R tyrosine kinase activity", Bioorg. Med. Chem. Lett., 7, 4, 421-424 (1997).

Nair, M.D., et al., "3-Chloroisocarbostyril & Its Chlorination Products", Indian J. Chem., vol. 5, 467-470 (1967).

Namikawa, Kazuhiko et al., "Akt/Protein Kinase B Prevents Injury-Induced Motoneuron Death and Accelerates Axonal Regeneration," The Journal of Neuroscience, 20(8), 2875-2886 (2000).

Nezu, Y. et al., "Dimethoxypyrimidines as Novel Herbicides, part 1. Synthesis and Herbicidal Activity of Dimethoxyphanoxyphenoxypyrimidines and Analogues," Pestic. Sci., 47(2): 103-113 (1996).

Nezu, Y., et al., "Dimethoxypyrimidines as Novel Herbicides, part 2. Synthesis and Herbicidal Activity of O-Pyrimidinylasalicylates and Analogues," Pestic. Sci., 47(2): 115-124 (1996).

Nigg, E.A., "Mitotic Kinases as Regulators of Cell Division and its Checkpoints," Nat. Rev. Mol. Cell Biol., 2: 21-32 (2001).

Noell, C.W. et al., "Potential purine Antagonists. XX. The Preparation and Reactions of Some Methylthiopurines", J. Am. Chem. Soc., 81(22), 5997-6007 (1959).

Nomenclature found from http://www.cem.msu.edu/~reusch/VirtualText/nomen1.htm (last visited on Nov. 18, 2007).

Norman, M.H. et al., "Structure-Activity Relationships of a Series of Pyrrolo[3,2-d]pyrimidine Derivatives and Related Compounds as Neuropeptide Y5 receptor Antagonists," J. Med. Chem., 43(22), 4288-4312 (2000).

Nugent, R.A. et al., "Pyrimidine Thiotheters: A Novel Class of HIV-1 Reverse Transcriptease Inhibitors with Activity Against BHAP-Resistant HIV", J. Med. Chem., 41, 3793-3803 (1998).

Okafor, Charles O., "Studies in the Heterocyclic Series. 1,3,9-Triazaphenothiazine Ring System, A New Phenothiazine Ring," J. Org. Chem., 40(19):2753-2755 (1975).

Parnell, E.W., "2-Cyano-4-nitrophenylhydrazine and 3-Amino-5-nitroindazole", J. Chem. Soc., 2363-2365 (1959).

Pei, J. et al., "Distribution, Levels and Activity of Glycogen Synthase Kinase-3 in the Alzheimer Disease Brain", J. Neuropathol. Exp. Neurology, 56, 70-78 (1997).

Prasad, G. et al., "18-Crown-6 as a catalyst in the dialkylation of o-nitrophenacyl derivatives," J. Org. Chem., 25, 7188-7190 (1991).

Raingeaud, J. et al., "MMK3- and MMK6-Regulated Gene Expression Is Mediated by p38 Mitogen-Activated Protein Kinase Signal Transduction Pathway," Mol. Cell. Biol. 16, 1247-1255 (1996).

Rogers, E., et al., "The aurora kinase AIR-2 functions in the release of chromosome cohesion in Caenorhabditis elegans meiosis," J. Cell Biol., 157(2): 219-229 (2002).

Rosen, N. et al., "Analysis of pp60src Protein Kinase Activity in Human Tumor Cell Lines and Tissues," J. Biol. Chem., 261, 13754-13759 (1986).

Rouse, J. et al., "A Novel Kinase Cascade Triggered by Stress and Heat Shock That Stimulates MAPKAP Kinase-2 and Phosphorylation of the Small Heat Shock Proteins," Cell, 78, 1027-1037 (1994).

Rueeger, H. et al, "Design, synthesis and SAR of a series of 2-substituted 4-amino-quinazolineneuropeptide Y Y5 receptor antagonists," Bioor. Med. Chem. lett., 10(11), 1175-1180 (2000).

Shikhaliev, K.S. et al., "Heterocyclization of quinazol-2-ylguanidines. 1. Reaction with amino acids", Chem. Heterocycl. Compd. 35 (7), 818-820 (1999).

Simone, J.V., "Oncology Introduction" in Cecil Textbook in Medicine, 20th ed. vol. 1, 1004-1010 (1996).

Singh, S.P. et al., "Synthesis & Mass Spectra of Some Substituted 2-(2'-Benzazolylamino)pyrimidines", Indian J. Chem. Sect. B, 22(1): 37-42 (1983).

Singhal, N. et al., "Synthesis and Antimalarial Activity of Some New Quinazoline Derivatives", Indian Chem. Soc. 61, 690-693 (1984).

Sivaraman, V.S. et al., "Hyperexpression of Mitogen-activated Protein Kinase in Human Breast Cancer", J. Clin. Invest., 99(7), 1478-1483 (1997).

Soriano, P. et al., ed Disruption of the C-SRC Proto-Ocogene Leads to Osteopetrosis in Mice, Cell, 64: 693-702 (1991).

Staley, C.A. et al., "Decreased Tumorigenicity of a Human Colon Adenocarcinoma Cell Line by an Antisense Expression Vector Specific for c-Src," Cell Growth Diff., 8 269-274 (1997).

Suzuki, S. et al., "Application of electrogenerated triphenylmethyl anion as a base for alkylation of arylacetic esters and arylacetonitrites and isomerization of allylbenzenes," Can. J. Chem., 72(2): 357-361 (1994).

Takashima, K. et al., "Tau Protein Kinase I is Essential for Amyloid β-Protein-Induced Neurotoxicity," PNAS 90, 7789-7793 (1993).

Takayanagi, H. et al., "Suppression of arthritic bone destruction by adenovirus-mediated csk gene transfer to synoviocytes and osteoclasts," J. Clin. Invest., 104, 137-146(1999).

Talamonti, M.S. et al., "Increase in activity and level of pp60c-src in progressive stages of human colorectal cancer," J. Clin Invest., 91(1): 53-60 (1993).

Tanaka, T.U. et al., "Evidence that the IpI1-Sli15 (Aurora Kinase—INCENP) Complex Promotes Chromosome Bi-orientation by Altering Kinetochore-Spindle Pole Connections," Cell, 108, 317-329 (2002).

Tanji, K. et al., "Purines. X. Reactivities of Methyl Groups on 9-Phenylpurines: Condensation with an Aldehyde or an Ester, and Oxidation with Selenium Dioxide," Chem. Phar. Bull., 40 (1), 227-229 (1992).

The Condensed Chemical Dictionary, Sixth Edition h Rose, 38 by Arthur and Elizabeth Rose, 38 (1961).

Ti, J. et al., "Anticancidal activity of pyrimidine-peptide conjugates," J. Med. Chem., 23(8), 913-918 (1980).

Toriyabe, Keiji et al., "Preparation of sulfur-containing arylthiazoles and insecticides," Chemica Abstracts, 132(8): 93314 (2000).

Traxier P. et al., "Use of a pharmacophonre model for the design of EGF-R Tyrosine Kinase Inhibitors: 4-(Phenylamino)Pyrazolo[3,4-d]pyrimidines," Journal of Medicinal Chemistry, 40(22): 3601-3616 (1997).

Venugopalan, B. et al., "Synthesis and antimalarial activity of pyrido 3,2-f)quinozalines and their N-oxides," Indian J. Chem. Sect. B, 34, 9, 779-790 (1995).

Wagman, A.S. et al., "Discovery and Development of GSK3 Inhibitors for the Treatment of Type 2 Diabetes," Current Pharmaceutical Design, 10, 1105-1137 (2004).

Warner, S.L. et al., "Targeting Aurora-2 Kinase in Cancer," Mol. Cancer Thera., 2, 589-585, 2003.

Whelchel, A. et al., "Inhibition of ERK Activation Attenuates Endothelin-stimulated Airway Smooth Muscle Cell Proliferation," Am. J. Respir. Cell Mol. Biol., 16, 589-596 (1997).

Wiener, J.R., "Decreased Src Tyrosine Kinase Activity Inhibits Malignant Human Ovarian Cancer Tumor Growth in a Nude Mouse Model," Clin. Cancer Res., 5, 2164-2170 (1999).

Wolft, Manfred E., "Burger's Medicinal Chemistry, 1" 5th ed., Part 1" John Wiley & Sons, 1995, pp. 975-977.

Yuan, Z.Q. et al., "Frequent activation of AKT2 and induction of apoptosis by inhibition of phosphoinositide-3-OH kinase/Akt pathway in human ovarian cancer," Oncogene, 19, 2324-2330 (2000).

Zhang, Z. et al., "Destabilization of β-catenin by mutations in presenilin-1 potentiates neuronal apoptosis," Nature, 395, 698-702 (1998).

Office Action from U.S. Appl. No. 10/026,992, mailed May 22, 2008.
Vishweshwar, P. et al., "Crystal engineering of pharmaceutical co-crystals from polymorphic active pharmaceutical ingredients," Chemical Communications 20050928 GB, No. 36, Sep. 28, 2005, pp. 4601-4603.
Almarsson et al., "Crystal engineering of the composition of pharmaceutical phases. Do phamaceutical co-crystals represent a new path to improved medicines," Chemical Communications—Chemcom, Royal Society of Chemistry, GB, Jan. 1, 2004, pp. 1889-1896.
Revill, P. et al., "Telaprevir: HCV NS3 protease inhibitor treatment of hepatitis C," Drugs of the Future, Prous Science, Es, vol. 32, No. 9, Jan. 1, 2007, pp. 788-798.
International Search Report, PCT/US2009/055384, filed Feb. 8, 2010.
Agarwal, N. et al., "Suitably Functionalized Pyrimidines as Potential Antimycotic Agents", Bioorg. Med. Chem. Ltt., 10, 8, 703-706 (2000).
Ali, N.m. et al., "Palladium-Catalyzed Cross Coupling Reactions of Arylboronic Acids with Pi-Deficient Heteroaryl Chlorides" Tetrahedron, 48 (37), 8117-8126 (1992).
Alonso, M. et al., "GSK-3 Inhibitors: Discoveries and Developments", Current Medicinal Chemistry, 11, 755-763 (2004).
Anderson, Neil G. "Requirement for integration of signals from two distinct phosphorylation pathways for activation of MAP kinase." Nature, 343, 651-653 (1990).
Anonymous, "Vertex Inhibitors of Aurora-2, glycogen synthase kinase-3 and Src Kinase", Expert Opin. Ther. Patents 14(3): 439-443 (2004).
Bai, G.U. et al., "Triazines and Related Products. Part 28' Conversion of 3-Aryl-I-(2-cyanophenyl) triazenes into 3-Arlquinazolin-4(3H)-ones with Formamide" J. Chem. Soc. Perkin Trans. I, 2765-2766 (1984).
Baig, Ghouse Unissa et al. "Triazines and related products. Part 27. Thermolysis of 4-anilino-1,2,3-benzotriazines," J. Chem., Soc., Perkin Trans. 1(5): 999-1003 (1984).
Banker, G.S. et al., "Modern Pharmaceutics", 34d ed., Marcel Dekker, New York 1996, pp. 451& 596.
Biagi, G. et al., Synthesis of 4,6-Distributed and 4,5,6-Trisubstituted-2-Phyl-pyrimidines and their Affinity Towards A1 Adenosine Receptors, IL Farmaco., 52(1), 61-65 (1997).
Biscardi, J.S. et al., "c-Src, Receptor Tyrosine Kinases, and Human Cancer", Adv. Cancer Res., 76, 61 (1999).
Bischoff, J.R. et al., "A homologue of Drosophila aurora kinase is oncogenic and amplified in human colorectal cancers", The EMBO Journal, 17(11): 3052-3065 (1998).
Bischoff, J.R., et al., "The Aurora/IpI1p kinase family: regulators of chromosome segregation and cytokinesis", Cell Biology, 9, 454-459 (1999).
Bjorbaek, c. et al., "Divergent Functional Roles for p90rsk Kinase Domains", J. Biol. Chem., 270(32, 19948-19552 (1995).
Bokemeyer, D. et al., "Multiple intracellular MAP kinase signaling cascades", Kidney Int., 49, 1187-1198 (1996).
Bolen, J.B. et al., "Activation of pp60c-src protein kinase activity in human colon carcinoma", PNAS, 84, 2251-2255 (1987).
Boschelli et al., "Small molecule inhibitors of Src family kinases", Drugs of the Future, 25(7):717-736 (2000).
Brownlees J. et al., "Tau phosphorylation in transgenic mice expressing glycogen synthase kinase-3beta transgenes", Neuroreport., 8(15), 3251-5 (1997).
Brunswick, D.J. et al., "Cyclic Amidines. Part XXII. Novel Isomerism of Disubstituted Tricyoquinazolines and Molecular Orientations in Carcinogenesis", J. Chem. Soc. (3), 2641-2647 (1970).
Campbell, S.F. et al., "2,4-Diamino-6,7-dimethoxyquinazolines. 3.2(4-Heterocyclylpiperazin-I-yl) Derivatives as α1-Adrenoceptor Antagonists and Antihypertensive Agents," J. Med Chem., 30, 1794-1798 (1987).
CAPLUS listing Accession No. 1994:292136, Nakajima, Y. et al., "Pyrazoles agricultural and horticultural bactericides," JP 06065237 (1994).
Casanova, B. et al., "Revision critica de la patogenia actual de la esclerosis multiple y futuras direcciones posibles," Rev. Neurol., 28 (9): 909-915 (1999).

Chalmers, D.T., et al., "Corticotrophin-releasing factor receptors: from molecular biology to drug design," TiPS, 17, 769-776 (2001).
Charpiot, B. et al., "Quinazolines: Combined type 3 and 4 phosphodiesterase inhibitors", Bioorg. Med. Chem. Lett., 8 (20), 2891-2896 (1988).
Chen, R.H. et al., "Phosphorylation of the c-Fos transrepression domain by mitogent-activated protein kinase and 90-kDa ribosomal S6 kinase", Proc. Natl. Acad. Sci. USA, 90, 10952-10956 (1993).
Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Coghlan, M.P. et al., "Selective small molecule inhibitors of glycogen synthase kinase-3 modulate glycogen metabolism and gene transcription", Chemistry & Biology, 7, 793-803 (2000).
Cohen, P. et al., "The renaissance of GSK3," Nat. Rev. Mol. Cell Biol., 2, 769-776 (2001).
Cohen, P. "Dissection of the Protein Phosphorylation Cascades Involved in Insulin and Growth Factor Action", Biochem. Soc. Trans., 21-555-567 (1993).
Coleman, R.A., "The Biological Evaluation of New Compounds" in Medicinal Chemistry: Principles and Practice, king, Frank D. ed, Royal Society of Chemistry, 53-66 (1994).
Crespo, M.I,. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).
Crews, C.M. et al., "The Primary Structure of MEK, a Protein Kinase That Phosphorylates the ERK Gene Product", Science, 258, 478-480 (1992).
Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).
Curd, F.H.S. et al., "Synthetic antimalarials. Part XVII. Some aminoalkylaminoquinoline derivatives", J. Chem. Soc. 899-909 (1947).
D'Atri, G. et al., "Novel pyrimidine and 1,3,5-triazine hypolipemic agents", J. Med. Chem. 27(12), 1621-1629 (1984).
Damasio, A.R., "Alzheimer's Disease and Related Dementias," in Cecil Textbook of Medicine, 20th ed., 2:1992-1996 (1996).
Douglas, et al., "Introduction to Viral Disease" in Cecil Textbook of Medicine, 20th Ed., vol. 2, 1739-1749 (1996).
Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).
Fedorynski, M. et al., "Synthesis of 1-Arycyclopropanecarbonitriles under Phase-transfer Cataylist Conditions", Org. Prep. Proced. Int., 27(3), 355-359 (1995).
Fischer, P.M. et al., "Inhibitors of Cyclin-Dpendent Kinases as Anti-Cancer Therapeutics", Current Med. Chem., 7, 1213-1245 (2000).
Fischer A., "Therapeutic Strategies in Alzheimer's Disease: M1 Muscarinic Agonists," Jpn. J. Pharmacol., 84(2):101-12 (2000).
Fox T. et al. "A single amino acid substitution makes ERK2 susceptible to pyridinyl imidazole inhibitors of p38 MAP kinase", Protein Sci., 7:2249-2255 (1998).
Frame, M.C., "Src in cancer: deregulation and consequences for cell behaviour," Biochimica et Biophysica Acta, 1602, 114-130 (2002).
Frampton, J.E. et al., "Pentoxifyline (Oxpentifylline)—A Review of its Therapeutic Efficacy in the Management of Peripheral Vascular and Cerebrovascular Disorder," Drugs & Aging, 7(6): 480-503 (1995).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).
Fry, d.W. et al., "Inhibitors of cyclin-dependent kinases as therapeutic agents for the treatment of cancer", Current Opin. Oncol. Endoc. & Metab. Investig., 2-40-59 (2000).

Ganellin, C.R., "Past Approaches to Discovering New Drugs as Medicines" in Medicinal Chemistry, Principles and Practices. King, Frank D. ed, Royal Society of Chemistry, 189-205 (1994).

Garigipati, R.S., "An efficient conversion of nitriles to amidines", Tetrahedron Lett., 31(14)., 1969-1972 (1990).

Gerschon, H. et al., "Pyrimidines 7. A Study of the Chlorination of Pyrimidines with Phosphorous Oxychloride in the Presence of N,N-Dimethylaniline", J. Heterocyclic Chem., 21, 1161-1167 (1984).

Glossary of Class Names of Organic Compounds and Reactive Intermediates Based on Structure found from http://www.chem.qmul.ac.uk/iupac/class/index.html (last visited on Nov. 18, 2007).

Gnecco, D. et al., "An Improved Preparation of 1-Methyl-4-Cyano-4-phenylpiperidine", Org. Prep. Proced. Int., 18 (4), 478-480 (1996).

* cited by examiner

CO-CRYSTALS AND PHARMACEUTICAL FORMULATIONS COMPRISING THE SAME

CROSS-REFERENCE TO RELATED APPLICATIONS

This application is a continuation of PCT Application Number PCT/US2009/055384, filed Aug. 28, 2009 which claims priority to U.S. Provisional Application Ser. No. 61/093,972 and U.S. Provisional Application Ser. No. 61/093,942, both filed Sep. 3, 2008, the contents of which are incorporated herein by reference in their entirety.

BACKGROUND OF THE INVENTION

Hepatitis C virus (HCV) is estimated to infect 170 million people worldwide [Purcell, R. H., *Hepatitis C virus: historical perspective and current concepts*. FEMS Microbiology Reviews, 1994. 14: p. 181-192.] Nearly four million individuals may be infected in the United States alone [M. J. Alter et al., "The Epidemiology of Viral Hepatitis in the United States, *Gastroenterol. Clin. North Am.*, 23, pp. 437-455 (1994); M. J. Alter "Hepatitis C Virus Infection in the United States," *J. Hepatology*, 31, (Suppl. 1), pp. 88-91 (1999)].

VX-950 is a competitive, reversible peptidomimetic hepatitis C virus ("HCV") NS3/4A protease inhibitor with a steady state binding constant (ki*) of 3 nM (and with a Ki of 8 nM) [See International Publication No. 02/018369]:

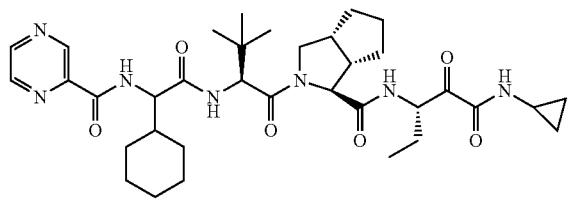

VX-950

In clinical trials, VX-950 has shown antiviral activity been shown to be an effective therapy against HCV, which is recognized as the causative agent for most cases of non-A, non-B hepatitis, with an estimated human sero-prevalence of 3% globally [A. Alberti et al., "Natural History of Hepatitis C," *J. Hepatology*, 31., (Suppl. 1), pp. 17-24 (1999)].

However, because VX-950 is practically insoluble in water, formulating it to be suitable for administration is difficult.

Therefore, there is a need for a pharmaceutical composition that provides improved forms in a co-crystal that includes VX-950 and maintains adequate levels of VX-950 concentration in the environment of use.

SUMMARY OF INVENTION

The present invention is directed to a pharmaceutical co-crystal that includes VX-950.

The present invention is also directed to a pharmaceutical formulation.

In one aspect, the present invention includes a pharmaceutical composition. The pharmaceutical composition includes an active ingredient and one or more excipients. In the pharmaceutical composition, the one or more excipients is present in an amount about at least 1% of the total weight of the formulation. The active ingredient comprises a co-crystal, which includes VX-950 and a co-former of 4-hydroxybenzoic acid.

In certain embodiments of the present invention, the co-crystal is present in amount of about 1 to 99% of the total weight of the formulation. In one embodiment, wherein the co-crystal is present in an amount at least about 10, 20, 30, 40, 50 or 60% of the total weight of the formulation. In one embodiment, the co-crystal is present in amount about at least 68% of the total weight of the formulation.

Typically, the co-crystal is present in an amount about at least 50% of the total weight of the formulation. In one embodiment, the co-crystal is present in an amount about at least 60% of the total weight of the formulation. In another embodiment, the co-crystal is present in an amount about at least 65% of the total weight of the formulation. In yet another embodiment, the crystalline composition is present in an amount about at least 70%, 75%, 80%, 85%, 90% or 95% of the total weight of the formulation.

In certain embodiments, the molar ratio of VX-950 included in the co-crystal with respect to the co-former is about 1:1.

In certain embodiments, the one or more excipients is selected from the group consisting of a filler, a surfactant, a glidant, a lubricant and a disintegrant.

In certain embodiments, the one or more excipients includes one or more fillers. Examples of the fillers can include, but are not limited to, the following: mannitol, lactose, sucrose, dextrose, maltodextrin, sorbitol, xylitol, powdered cellulose, microcrystalline cellulose, silicified microcrystalline cellulose, methylcellulose, ethylcellulose, hydroxyethylcellulose, methylhydroxyethylcellulose, talc, starch, pregelatinized starch, dibasic calcium phosphate, calcium sulfate and calcium carbonate. In some embodiments, the one or more fillers is microcrystalline cellulose, lactose or a combination thereof. In some embodiments, the one or more fillers are microcrystalline cellulose and lactose. I In certain embodiments, the one or more excipients includes one or more disintegrants. Examples of the disintegrants can include, but are not limited to, the following: croscarmellose sodium, sodium alginate, calcium alginate, alginic acid, starch, pregelatinized starch, sodium starch glycolate, crospovidone, cellulose and its derivatives, carboxymethylcellulose calcium, carboxymethylcellulose sodium, soy polysaccharide, guar gum, an ion exchange resin, an effervescent system based on food acids and an alkaline carbonate component, and sodium bicarbonate. In one embodiment, the one or more disintegrants is croscarmellose sodium.

In certain embodiments, the one or more excipients can include one or more surfactants. Examples of the surfactants may include, but are not limited to, sodium lauryl sulfate, docusate sodium, polyoxyethylene sorbitan fatty acid esters (e.g., polysorbate 20, 40, 60 and 80), polyoxyethylene 20 stearyl ethers, polyoxyethylene alkyl ethers, polyoxyethylene castor oil derivatives (e.g., polyoxyl 35 castor oil, polyoxyl 40 hydrogenated castor oil), pegylated hydrogenated castor oils, sorbitan esters of fatty acids (e.g., sorbitan monooleate, sorbitan monopalmitate, sorbitan monostearate, sorbitan tristearate etc.), Vitamin E or tocol derivatives, vitamin E TPGS, tocopheryl esters, lecithin, phospholipids and their derivatives, poloxamers (e.g., poloxamer 407, poloxamer 388, poloxamer 188), stearic acid, oleic acid, oleic alcohol, cetyl alcohol, mono and diglycerides, propylene glycol esters of fatty acids, glycerol esters of fatty acids (e.g., glycerol monooleate, glycerol monostearate), ethylene glycol palmitostearate, polyoxylglycerides (pegylated glycerides, e.g., labrafils, labrasol, gelucires etc.), propylene glycol monocaprylate, propylene glycol monolaurate, polyglyceryl oleate etc. In one embodiment, the one or more surfactants is sodium lauryl sulfate.

In certain embodiments, the one or more excipients can include one or more glidants. Examples of the glidants may include, but are not limited to, talc, colloidal silica (e.g., Cabosil M-5), magnesium oxide, magnesium silicate, leucine and starch. In one embodiment, the one or more glidants is colloidal silica.

In certain embodiments, the one or more excipients can include one or more lubricants. Examples of the lubricants may include, but are not limited to, talc, fatty acid, stearic acid, magnesium stearate, calcium stearate, sodium stearate, glyceryl monostearate, sodium lauryl sulfate, sodium stearyl fumarate, hydrogenated oils, fatty alcohol, fatty acid ester, glyceryl behenate, mineral oil, vegetable oil, leucine, sodium benzoate, or a combination thereof. In another embodiment, the one or more lubricants is sodium stearyl fumarate.

In one embodiment, the formulation comprises about 5 wt. % to 99 wt. % of the co-crystal, about 5 wt. % to 60 wt. % of a first filler, about 5 wt. % to 60 wt. % of a second filler, about 1 wt. % to 30 wt. % of a disintegrant, about 1 wt. % to 30 wt. % of a surfactant, about 1 wt. % to 30 wt. % of a lubricant, and about 1 wt. % to 30 wt. % of a glidant.

In one embodiment, The formulation comprises about 50 wt. % to 75 wt. % of the co-crystal, about 5 wt. % to 15 wt. % of a first filler, about 5 wt. % to 15 wt. % of a second filler, about 1 wt. % to 10 wt. % of a disintegrant, about 0.1 wt. % to 10 wt. % of a surfactant, about 0.1 wt. % to 10 wt. % of a lubricant, and about 0.1 wt. % to 10 wt. % of a glidant.

In one embodiment, the formulation comprises about 67.80 wt. % of the co-crystal, about 11.71 wt. % of a first filler, about 11.71 wt. % of a second filler, about 3 wt. % of a disintegrant, about 2 wt. % of a surfactant, about 0.78 wt. % of a glidant, and about 3 wt. % of a lubricant.

In certain embodiments, the formulation is in a form of a capsule, tablet, pill, powder, granule, aqueous suspension or solution. In one embodiment, the formulation is in a form of a capsule. Alternatively, in one embodiment, the formulation is in a form of a tablet. In another embodiment, the tablet is coated. In one embodiment, the formulation is an immediate release formulation.

The present invention also includes a method of formulating an active ingredient comprising VX-950 and 4-hydroxybenzoic acid. The method comprises steps of:
  providing the active ingredient; and
  blending the active ingredient with one or more excipients, forming a blended mixture.

In certain embodiments, the method further includes a step of processing the blended mixture.

In certain embodiments, the method further includes a step of lubricating the blended mixture.

In one embodiment, processing the blended mixture comprising granulating the blended mixture. In one embodiment, granulating the blending mixture comprises:
  dry granulating the blended mixture;
  wet granulating the blended mixture;
  high-shear granulating the blended mixture;
  fluid-bed granulating the blended mixture; or
  a combination thereof.

In one embodiment, granulating the blended mixture comprises dry granulating the blended mixture. In one embodiment, dry granulating the blended mixture comprises roller-compacting the blended mixture.

In certain embodiments, the method further includes milling the roller-compacted mixture, resulting in granules. In certain embodiments, the method further includes lubricating the granules.

In certain embodiments, the method further includes a step of compressing the lubricated granule mixture into a tablet.

In certain embodiments, the method further includes a step of coating the tablet.

In certain embodiments, the molar ratio of VX-950 with respect to 4-hydroxybenzoic acid ranges from about 5:1 to about 1:5. In one embodiment, the molar ratio of VX-950 with respect to 4-hydroxybenzoic acid ranges from about 1:1.

In certain embodiments, the step of providing the co-crystal active ingredient comprising VX-950 and 4-hydroxybenzoic acid includes controlling the particle size of the co-crystal. In some embodiments, controlling the particle size of the co-crystal includes reducing the particle size of the co-crystal. In some embodiments, controlling the particle size of the co-crystal comprises:
  a) crushing the co-crystal;
  b) sieving the co-crystal;
  c) milling the co-crystal; or
  e) a combination thereof.

Examples of milling the co-crystal includes, but not limited to, fitzmilling, co-milling, jet-milling, wet-milling, and nano-milling.

In certain embodiments of the method, providing the active ingredient comprising VX-950 and 4-hydroxybenzoic acid comprises preparing a solution of VX-950 separately from a solution of 4-hydroxybenzoic acid. In some embodiments, preparing a solution of VX-950 separately from a solution of 4-hydroxybenzoic acid comprises:
  a) preparing the solution of VX-950 in a first solvent and
  b) preparing the solution of 4-hydroxybenzoic acid in a second solvent.

In some embodiments, preparing a solution of VX-950 separately from a solution of 4-hydroxybenzoic acid further includes combining the solutions of the VX-950 and 4-hydroxybenzoic acid. In one embodiment, the first solvent and the second solvent are independently selected from the group consisting of diethyl ether, methyl tert-butyl ether, 2-methyl-tertahydrofuran, tetrahydrofuran, methyl acetate, ethyl acetate, isopropyl acetate, isobutyl acetate, tert-butyl acetate, acetone, 2-butanone, methyl iso-butyl ketone, dichloromethane, chloroform, dichloroethane, acetonitrile butyronitrile, toluene and benzene. In one embodiment, the first solvent is dichloromethane, and the second solvent is and tert-butyl methyl ether, acetonitrile or ethyl acetate. In one embodiment, the ratio of the first solvent with respect to the second solvent ranges from about 2:1 to about 1:5.

In certain embodiments, providing the active ingredient comprising VX-950 and 4-hydroxybenzoic acid comprises dissolving in a mixture of two or more solvents. In some embodiments, the mixture of two or more solvents comprises two or more solvents selected from the group consisting of diethyl ether, methyl tert-butyl ether, 2-methyltertahydrofuran, tetrahydrofuran, methyl acetate, ethyl acetate, isopropyl acetate, isobutyl acetate, tert-butyl acetate, acetone, 2-butanone, methyl iso-butyl ketone, dichloromethane, chloroform, dichloroethane, acetonitrile butyronitrile, toluene and benzene. In some embodiments, the mixture of two or more solvents comprises dichloromethane and tert-butyl methyl ether. In some embodiments, the ratio of dichloromethane to tert-butyl methyl ether ranges from about 2:1 to about 1:5. In some embodiments, the method further includes adding an anti-solvent. In one embodiment, the method further includes a step of adding an anti-solvent. In another embodiment, the anti-solvent includes tert-butyl methyl ether, heptane, acetonitrile, and ethylacetate.

In one embodiment, the step of providing the active ingredient includes seeding the mixture of the two or more solvents with the active ingredient.

In certain embodiments, the step of blending the active ingredient with one or more excipients comprises blending the one or more excipients selected from a filler, a surfactant, a glidant, a lubricant and a disintegrant.

In another aspect of the present invention, the present invention provides a method of treating HCV infection in a subject that comprises administering the subject a formulation. The formulation comprises an active ingredient, and one or more excipients present in an amount about at least 1% of the total weight of the formulation. The active ingredient comprises a co-crystal, which includes VX-950 and a co-former of 4-hydroxybenzoic acid.

In certain embodiments, the method further includes a step of administering an additional agent selected from an immunomodulatory agent; an antiviral agent; another inhibitor of HCV NS3/4A protease; another inhibitor of IMPDH; an inhibitor of a target in the HCV life cycle other than NS3/4A protease; an inhibitor of internal ribosome entry, a broad-spectrum viral inhibitor; a cytochrome P-450 inhibitor; or combinations thereof.

DETAILED DESCRIPTION OF THE INVENTION

Figure 1:
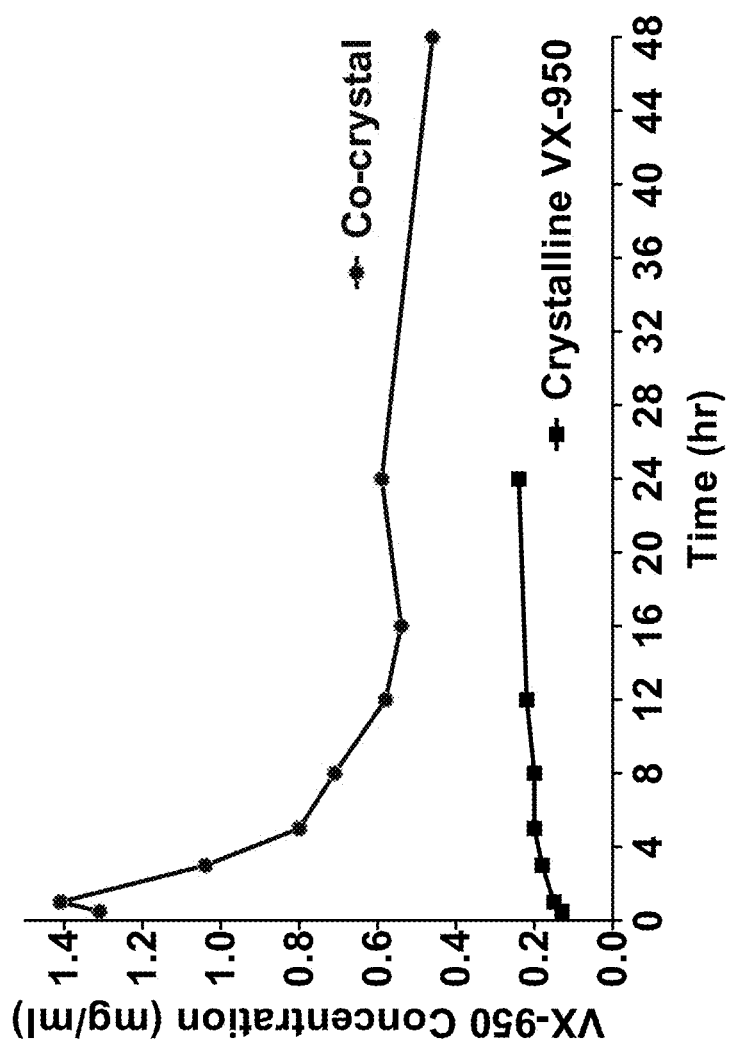
FIG. 1 shows kinetic solubility data of crystalline VX-950 compared to VX-950:4-hydroxybenzoic acid co-crystal in 1% sodium lauryl sulfate (SLS) media under supersaturated conditions.

It must be noted that as used herein and in the claims, the singular forms "a," "an," and "the" include plural referents unless the context clearly dictates otherwise. Thus, for example, reference to "a binder" includes two or more binders; reference to "a pharmaceutical agent" includes two or more pharmaceutical agents, and so forth.

As used herein, the term "active agent," "active pharmaceutical ingredient" or "API" refers to a pharmaceutically active agent or a drug, and all these terms may be used interchangeably. Furthermore, these terms can also refer to a co-crystal that includes VX-950 specifically.

The term "co-crystal" as used herein means one unique solid form of a crystalline material comprised of two or more unique compounds, the two or more unique compounds forming a new chemical entity. The co-crystal is a solid at room temperature, and has physically and chemically distinct characteristics from each of the two or more unique compounds. As mentioned above, co-crystals of this invention can be analyzed by methods known in the art for characterizing solid or crystalline materials. Examples of characterization methods include thermogravimetric analysis (TGA), differential scanning calorimetry (DSC), X-ray powder diffraction (XRPD), solubility analyses, dynamic vapor sorption, infrared off-gas analysis, and suspension stability. TGA can be used to investigate the presence of residual solvents in a co-crystal sample, and to identify the temperature at which decomposition of each co-crystal sample occurs. DSC can be used to look for thermo-transitions occurring in a co-crystal sample as a function of temperature and determine the melting point of each co-crystal sample. XRPD can be used for structural characterization of the co-crystal. Solubility analysis can be performed to reflect the changes in the physical state of each co-crystal sample. And suspension stability analysis can be used to determine the chemical stability of a co-crystal sample in a solvent. Described in great detail are some of such methods.

The co-crystals of the present invention comprise a co-former non-covalently bound to an API (i.e., VX-950). For example, the co-former may be H-bonded directly to the API or may be H-bonded to an additional molecule which is bound to the API. The additional molecule interacts with the API non-covalently. The additional molecule can also be a different API. Solvates of API compounds that do not further comprise a co-former are not co-crystals according to the present invention. The co-crystals may however, include one or more solvent molecules in the crystalline lattice. That is, solvates of co-crystals, or a co-crystal further comprising a solvent or compound that is a liquid at room temperature, is included in the present invention, but crystalline material comprised of only one solid and one or more liquids (at room temperature) are not included in the present invention, with the previously noted exception of specifically stated liquid APIs. The co-crystals may also be a co-crystal between a co-former and a salt of an API, but the API and the co-former of the present invention are constructed or bonded together through hydrogen bonds. Other modes of molecular recognition may also be present including, pi-stacking, guest-host complexation and van der Waals interactions. Of the interactions listed above, hydrogen-bonding is the dominant interaction in the formation of the co-crystal, (and a required interaction according to the present invention) whereby a non-covalent bond is formed between a hydrogen bond donor of one of the moieties and a hydrogen bond acceptor of the other. Hydrogen bonding can result in several different intermolecular configurations. For example, hydrogen bonds can result in the formation of dimers, linear chains, or cyclic structures. These configurations can further include extended (two-dimensional) hydrogen bond networks and isolated triads.

The term "co-former" is a pharmacologically inert molecule that alters the crystal form of a solid drug through the formation of co-crystals, clathrates or other crystalline solid forms.

The term "immediate release" means any type of release of the active ingredient such as VX-950 from the composition of the present invention resulting in in vitro or in vivo release over a short period of time, (e.g., less than one hour) sufficient to provide therapeutically effective plasma levels over similarly short time interval and/or to modify other pharmacokinetic properties of the active ingredient. The immediate release formulations of the present invention can be tested in an appropriate environment of use to measure the amount of the active ingredient released.

As used herein, an "environment of use" can be either the in vivo environment, such as the GI tract of an animal, particularly a human, or the in vitro environment of a test solution, such as appropriate dissolution media (e.g., phosphate buffered saline solution, 1% sodium lauryl sulfate, fed or fasted simulated gastric or intestinal media).

The term "excipient" herein includes any substance used as a vehicle for delivery of the active ingredient to a subject, and any substance added to the active ingredient, for example to improve its handling properties or to permit the resulting composition to be formed into an orally deliverable unit dose having the desired shape and consistency. Excipients can include, by way of illustration and not by limitation, a filler, a binder, a surfactant, a disintegrant, a glidant, a lubricant or a combination thereof, dyes, substances added to improve appearance of a dosage form, and any other substance other than the active ingredient conventionally used in the preparation of oral dosage forms.

The term "bioavailability" herein relates to a measure of the amount of active ingredient that is absorbed via the gastrointestinal tract into the bloodstream. More specifically, "bioavailability" is used herein to denote dose-normalized $AUC_{(0-\infty)}$ for a specific orally administered composition expressed as a percentage of dose-normalized $AUC_{(0-\infty)}$ for the active ingredient delivered intravenously at the same dosage rate. The make-up of the formulation can influence bioavailability of the active ingredient. While two formulations may use the identical active ingredient, the bioavailability of the active ingredient may not be the same. As such, bioavailability of an active ingredient can vary significantly depending on the make-up of a formulation, for example, the ingredients of excipients and their amounts and grade.

The term "processing" means preparing, treating or converting a material with the aim of readying for some purpose.

"Anti-solvent" is a suitable solvent or combination of solvents capable of initiating that compound's precipitation from solution.

In certain embodiment, the immediate release composition of the present invention is designed to provide for immediate release of an active ingredient containing a co-crystal that includes VX-950 upon exposure to a use environment, such as gastric fluid, upon administration. The immediate release composition of the present invention provides for both rapid dissolution of the active ingredient upon introduction of the composition to an aqueous environment, and for a rapid rise in plasma concentration of the practically insoluble active ingredient to therapeutic levels following administration to a subject.

It has been found that the co-crystal that includes VX-950 and a co-former of 4-hydroxybenzoic acid give rise to improved properties, as compared to VX-950 in a free form (including free acids, free bases, and zwitter ions, hydrates, solvates, etc.), particularly with respect to, but are not limited to: solubility, dissolution, bioavailability, stability, $C_{max}$, $T_{max}$, and processability. For example, a co-crystal that includes VX-950 is advantageous where the free form of crystalline VX-950 is very slightly soluble in water. Additionally, the co-crystal properties conferred upon the API are also useful because the bioavailability of the API can be improved and the plasma concentration and/or serum concentration of the API can be improved. This is particularly advantageous for orally-administrable formulations. Moreover, the dose response of the API can be improved, for example by increasing the maximum attainable response and/or increasing the potency of the API by increasing the biological activity per dosing equivalent.

In preparing the co-crystal that includes VX-950 and the co-former of 4-hydroxybenzoic acid, VX-950 and 4-hydroxybenzoic acid are dissolved in an appropriate solvent system. In one embodiment, VX-950 and 4-hydroxy benzoic acid are dissolved independently in respective solvents and subsequently combined. In another embodiment, VX-950 and 4-hydroxy benzoic acid are dissolved together in a mixture of two or more solvents. Seeding can be facilitated formation of the co-crystal, providing better control (e.g., better morphology).

Example of the solvent systems for preparing the co-crystal including VX-950 may include, but are not limited to, ether solvents (e.g., diethyl ether, methyl tert-butyl ether, 2-methyltertahydrofuran, and tetrahydrofuran), acetate solvents (e.g., methyl acetate, ethyl acetate, isopropyl acetate, isobutyl acetate, and tert-butyl acetate), ketone solvents (e.g., acetone, 2-butanone, and methyl isobutyl ketone), alkylhalide solvents (e.g., dichloromethane, chloroform, and dichloroethane), nitrile solvents (e.g., acetonitrile and butyronitrile), or hydrocarbon solvents (e.g., toluene and benzene).

Examples of characterization methods include thermogravimetric analysis (TGA), differential scanning calorimetry (DSC), X-ray powder diffraction (XRPD), single crystal structure determination, solubility analyses, dynamic vapor sorption, infrared off-gas analysis, and suspension stability. TGA can be used to investigate the presence of residual solvents in a co-crystal sample, and to identify the temperature at which decomposition of each co-crystal sample occurs. DSC can be used to look for thermo-transitions occurring in a co-crystal sample as a function of temperature and determine the melting point of each co-crystal sample. XRPD and single crystal structure determination can be used for structural characterization of the co-crystal. Solubility analysis can be performed to reflect the changes in the physical state of each co-crystal sample. And suspension stability analysis can be used to determine the chemical stability of a co-crystal sample in a solvent.

In some embodiment, an effective amount is the amount which is required to confer a therapeutic effect on the treated subject, e.g., a patient. The effective amount of a co-crystal that includes VX-950 and the co-former is between about 0.1 mg/kg to about 150 mg/kg (e.g., from about 1 mg/kg to about 60 mg/kg). Effective doses will also vary, as recognized by those skilled in the art, dependent on route of administration, excipient usage, and the possibility of co-usage with other therapeutic treatments including use of other therapeutic agents and/or therapy.

The co-crystals or pharmaceutical compositions of this invention can be administered to the subject in need thereof (e.g., cells, a tissue, or a patient (including an animal or a human)) by any method that permits the delivery of the compound VX-950, e.g., orally, intravenously, or parenterally. For instance, they can be administered via pills, tablets, capsules, aerosols, suppositories, liquid formulations for ingestion or injection or for use as eye or ear drops, dietary supplements, and topical preparations.

In some embodiments, the present invention provides methods of controlling the particle size of the co-crystals. The particle size of the co-crystal disclosed herein can influence physical and chemical features (e.g., bioavailability) of the fomulations of the present invention. Depending on the type of machines (e.g., Jetmill® MC50 Jetpharma Micronizer) used to micronize the co-crystal, the particle size of the co-crystal can vary. Examples of controlling the particle sizes of the co-crystal can include, but are not limited to, the following: crushing the co-crystal, sieving the co-crystal, and milling the co-crystal. Examples of milling include, but not limited to, fitzmilling, co-milling, jet-milling, wet-milling, nano-milling, or a combination thereof.

In one embodiment, the pharmaceutical formulations of the present invention include one or more excipients. In certain embodiment, the one more excipients include one or more fillers.

The term "filler component" refers to one or more substances that act to dilute the API to the desired dosage and/or that act as a carrier for the API. In some embodiments of the pharmaceutical formulations, the first filler component comprises one or more filler substances. In some embodiments of the pharmaceutical formulations, the filler component comprises one or more diluent substances. In some embodiments of the pharmaceutical formulations, the first filler component comprises one or more substances that are diluents and fillers.

In some embodiments, the first filler component comprises at least one a substance that improves the mechanical strength and/or compressibility of the pharmaceutical compositions of the invention.

Examples of the filler components can include, but are not limited to, mannitol, lactose (e.g., Lactose—316 Fast-Flo), sucrose, dextrose, maltodextrin, sorbitol, xylitol, powdered cellulose, microcrystalline cellulose (e.g., Avicel PH113, PH101, PH102, etc.), silicified microcrystalline cellulose (e.g., Prosolv HD90), methylcellulose, ethylcellulose, hydroxyethylcellulose, methylhydroxyethylcellulose, talc, starch, pregelatinized starch, dibasic calcium phosphate, calcium sulfate and calcium carbonate.

In some embodiments of the pharmaceutical formulations, the first filler component is microcrystalline cellulose or lactose.

In some embodiments of the pharmaceutical formulations, the first filler component is microcrystalline cellulose.

In some embodiments of the pharmaceutical formulations, the first filler component is lactose.

In some embodiments of the pharmaceutical formulations, the one or more filler components are microcrystalline cellulose and lactose.

In some embodiments, the filler is present in an amount of about least 1, 2, 3, 4, 5, 6, 7, 8, 9, 10, 11, 12, 13, 14, 15, 20, 25, 30, 35, 40, 45 or 50% of the total weight of the formulation. In some embodiments of the pharmaceutical formulations, the first filler component comprises from about 0.01% to about 30% by weight of the pharmaceutical formulation. In some embodiments of the pharmaceutical formulations, the first filler component comprises from 5% to about 25% by weight of the pharmaceutical formulation. In some embodiments of the pharmaceutical formulations, the first filler component comprises from about 10% to about 20% by weight of the pharmaceutical formulation. In some embodiments of the pharmaceutical formulations, the first filler component comprises from about 10% to about 15% by weight of the pharmaceutical formulation. In some embodiments of the pharmaceutical formulations, the first filler component comprises from about 10% to about 14% by weight of the pharmaceutical formulation. In some embodiments of the pharmaceutical formulations, the first filler component comprises from about 10% to about 13% by weight of the pharmaceutical formulation. In some embodiments of the pharmaceutical formulations, the first filler component comprises from about 11% to about 13% by weight of the pharmaceutical formulation. In some embodiments of the pharmaceutical formulations, the first filler component comprises about 12% by weight of the pharmaceutical formulation.

In certain embodiments, the pharmaceutical compositions of the present invention comprise a first filler component and a second filler component.

In some embodiments of the pharmaceutical formulations, the first filler component and the second filler component combined comprise from about 0.01% to about 60% by weight of the pharmaceutical formulation. In some embodiments of the pharmaceutical formulations, the first filler component and the second filler component combined comprise from about 0.01% to about 40% by weight of the pharmaceutical formulation. In some embodiments of the pharmaceutical formulations, the first filler component and the second filler component comprise from about 0.5% to about 40% by weight of the pharmaceutical formulation. In some embodiments of the pharmaceutical formulations, the first filler component and the second filler component comprise from about 0.1% to about 40% by weight of the pharmaceutical formulation. In some embodiments of the pharmaceutical formulations, the first filler component and the second filler component comprise from about 1% to about 40% by weight of the pharmaceutical formulation. In some embodiments of the pharmaceutical formulations, the first filler component and the second filler component comprise from 5% to about 40% by weight of the pharmaceutical formulation. In some embodiments of the pharmaceutical formulations, the first filler component and the second filler component comprise from about 10% to about 35% by weight of the pharmaceutical formulation. In some embodiments of the pharmaceutical formulations, the first filler component and the second filler component comprise from about 10% to about 30% by weight of the pharmaceutical formulation. In some embodiments of the pharmaceutical formulations, the first filler component and the second filler component comprise from about 10% to about 25% by weight of the pharmaceutical formulation. In some embodiments of the pharmaceutical formulations, the first filler component and the second filler component comprise about 12% by weight of the pharmaceutical formulation. In some embodiments, the first filler component and the second filler component comprise from about 15% to about 25% by weight of the pharmaceutical formulation. In some embodiments, the first filler component and the second filler component comprise from about 17% to about 25% by weight of the pharmaceutical formulation. In some embodiments, the first filler component and the second filler component comprise from about 20% to about 25% by weight of the pharmaceutical formulation. In some embodiments, the first filler component and the second filler component comprise from about 23% by weight of the pharmaceutical formulation. In some embodiments, the first filler component and the second filler component comprise from about 23.42% by weight of the pharmaceutical formulation.

Examples of the disintegrants may include, but are not limited to, croscarmellose sodium (e.g., AcDiSol), sodium alginate, calcium alginate, alginic acid, starch, pregelatinized starch, sodium starch glycolate, crospovidone, carboxymethylcellulose calcium, cellulose and its derivatives, carboxymethylcellulose sodium, soy polysaccharide, guar gum, an ion exchange resin, an effervescent system based on food acids and an alkaline carbonate component, and sodium bicarbonate.

In some embodiments of the pharmaceutical formulations, the first disintegrant component is croscarmellose sodium.

In some embodiments of the pharmaceutical formulations, the first disintegrant component comprises an amount of about least 1, 2, 3, 4, 5, 6, 7, 8, 9, 10, 15, 20, 25, 30, 35 or 40% of the total weight of the formulation. In some embodiments of the pharmaceutical formulations, the first disintegrant component comprises from about 0.01% to about 30% by weight of the pharmaceutical formulation. In some embodiments, the first disintegrant component comprises from about 0.01% to about 20% by weight of the pharmaceutical formulation. In some embodiments, the first disintegrant component comprises from about 0.5% to about 20% by weight of the pharmaceutical formulation. In some embodiments, the first disintegrant component comprises from about 0.1% to about 20% by weight of the pharmaceutical formulation. In some embodiments, the first disintegrant component comprises from about 0.5% to about 15% by weight of the pharmaceutical formulation. In some embodiments, the first disintegrant component comprises from 0.5% to about 10% by weight of the pharmaceutical formulation. In some embodiments, the first disintegrant component comprises from about 0.5% to about 5% by weight of the pharmaceutical formulation. In some embodiments, the first disintegrant component comprises from about 1% to about 4% by weight of the pharmaceutical formulation. In some embodiments, the first disintegrant component comprises from about 1% to about 3% by weight of the pharmaceutical formulation. In some embodiments, the first disintegrant component comprises from about 2% to about 3% by weight of the pharmaceutical formulation. In some embodiments, the first disintegrant component comprises about 3% by weight of the pharmaceutical formulation. In some embodiments, the first disintegrant component comprises about 3% by weight of the pharmaceutical formulation.

In certain embodiments of the pharmaceutical formulations, the one more excipients include one or more surfactants. Surfactants may be used to enhance wettability of poorly soluble or hydrophobic compositions. The surfactants can include, but are not limited to, ionic surfactants, non-ionic surfactants or cationic surfactants. Examples of the surfactants may include, but are not limited to, sodium lauryl sulfate, docusate sodium, polyoxyethylene sorbitan fatty acid esters (e.g., polysorbate/Tween 20, 40, 60 and 80), polyoxyethylene 20 stearyl ethers (also known as the Brij series of surfactants; e.g., Brij 78, Brij 30, Brij 35, Brij 52, Brij 56, Brij 58, Brij 72, Brij 721, Brij 76, Brij 92, Brij 96, and Brij 98), polyoxyethylene alkyl ethers, polyoxyethylene castor oil derivatives (e.g., polyoxyl 35 castor oil e.g., CREMOPHOR® EL, polyoxyl 40 hydrogenated castor oil e.g., CREMOPHOR® RH40), pegylated hydrogenated castor oils, sorbitan esters of fatty acids (e.g., sorbitan monolaurate e.g., Span 20, sorbitan monooleate e.g., Span 80, sorbitan monopalmitate e.g., Span 40, sorbitan monostearate e.g., Span 60, sorbitan tristearate etc.), Vitamin E or tocol derivatives, vitamin E TPGS, tocopheryl esters, natural or synthesized lecithins, phospholipids and their derivatives, poloxamers(polyoxyethylene and polyoxypropylene copolymers, e.g., poloxamer 407, poloxamer 388, poloxamer 188), stearic acid, oleic acid, oleic alcohol, cetyl alcohol, mono and diglycerides, propylene glycol esters of fatty acids, glycerol esters of fatty acids (e.g., glycerol monooleate, glycerol monostearate), ethylene glycol palmitostearate, polyoxylglycerides (pegylated glycerides, e.g., labrafils, labrasol, gelucires etc.), propylene glycol monocaprylate, propylene glycol monolaurate, polyglyceryl oleate, or any combination of the herein above-mentioned surfactants.

In certain embodiment of the pharmaceutical formulations, the one or more surfactant is sodium lauryl sulfate.

In some embodiments of the pharmaceutical formulations, the one or more surfactant comprises an amount of about least 1, 2, 3, 4, 5, 6, 7, 8, 9, 10, 15, 20, 25, 30, 35 or 40% of the total weight of the formulation. In some embodiments of the pharmaceutical formulations, the one or more surfactants component comprises from about 0.01% to about 30% by weight of the pharmaceutical formulation. In some embodiments, the one or more surfactants component comprises from about 0.01% to about 20% by weight of the pharmaceutical formulation. In some embodiments, the one or more surfactants component comprises from about 0.5% to about 20% by weight of the pharmaceutical formulation. In some embodiments, the one or more surfactants component comprises from about 0.5% to about 15% by weight of the pharmaceutical formulation. In some embodiments, the one or more surfactants component comprises from 0.5% to about 10% by weight of the pharmaceutical formulation. In some embodiments, the one or more surfactants component comprises from about 0.5% to about 5% by weight of the pharmaceutical formulation. In some embodiments, the one or more surfactants component comprises from about 1% to about 4% by weight of the pharmaceutical formulation. In some embodiments, the one or more surfactants component comprises from about 1% to about 3% by weight of the pharmaceutical formulation. In some embodiments, the one or more surfactants component comprises from about 2% to about 3% by weight of the pharmaceutical formulation. In some embodiments, the one or more surfactants component comprises about 2% by weight of the pharmaceutical formulation. In some embodiments, the one or more surfactants component comprises about 2% by weight of the pharmaceutical formulation.

In certain embodiments, the one more excipients can include one or more lubricants. Suitable lubricants possess anti-sticking or anti-tacking properties. Examples of the lubricants may include, but are not limited to, talc, fatty acid, stearic acid, magnesium stearate, calcium stearate, sodium stearate, glyceryl monostearate, sodium lauryl sulfate, sodium stearyl fumarate, hydrogenated oils, fatty alcohol, fatty acid ester, glyceryl behenate, mineral oil, vegetable oil, leucine, sodium benzoate, or a combination thereof. In certain embodiment of the pharmaceutical formulations, the one or more lubricant is sodium stearyl fumarate.

In some embodiments of the pharmaceutical formulations, the one or more lubricant comprises an amount of about least 1, 2, 3, 4, 5, 6, 7, 8, 9, 10, 15, 20, 25, 30, 35 or 40% of the total weight of the formulation. In some embodiment, the one or more lubricant comprises from about 0.01% to about 30% by weight of the pharmaceutical formulation. In some embodiments, the one or more lubricant comprises from about 0.01% to about 20% by weight of the pharmaceutical formulation. In some embodiments, the one or more lubricant comprises from about 0.1% to about 20% by weight of the pharmaceutical formulation. In some embodiments, the one or more lubricant comprises from about 0.5% to about 5% by weight of the pharmaceutical formulation. In some embodiments, the one or more lubricant comprises from about 1% to about 5% by weight of the pharmaceutical formulation. In some embodiments, the one or more lubricant comprises from about 0.5% to about 4% by weight of the pharmaceutical formulation. In some embodiments, the one or more lubricant comprises from about 1% to about 3% by weight of the pharmaceutical formulation. In some embodiments, the one or more lubricant comprises about 3% by weight of the pharmaceutical formulation.

In certain embodiments, the one more excipients can include one or more glidants. Suitable glidants can improve the flow of a formulation, and may possess anti-sticking or anti-tacking properties. Examples of the glidants may include, but are not limited to, talc, colloidal silica (e.g., Cabosil M-5), magnesium oxide, magnesium silicate, leucine and starch or a combination thereof. In certain embodiment of the pharmaceutical formulations, the one or more glidant is colloidal silica.

In some embodiments of the pharmaceutical formulations, the one or more glidant component comprises from about 0.01% to about 30% by weight of the pharmaceutical formulation.

In some embodiments, the one or more glidant component comprises from about 0.01% to about 20% by weight of the pharmaceutical formulation. In some embodiments, the one or more glidant component comprises from about 0.25% to about 20% by weight of the pharmaceutical formulation. In some embodiments, the one or more glidant component comprises from about 0.25% to about 10% by weight of the pharmaceutical formulation. In some embodiments, the one or more glidant component comprises from about 0.25% to about 5% by weight of the pharmaceutical formulation. In some embodiments, the one or more glidant component comprises from 0.25% to about 3% by weight of the pharmaceutical formulation. In some embodiments, the one or more glidant component comprises from about 1% to about 3% by weight of the pharmaceutical formulation. In some embodiments, the one or more glidant component comprises from about 2% to about 3% by weight of the pharmaceutical formulation. In some embodiments, the one or more glidant component comprises about 3% by weight of the pharmaceutical formulation. In some embodiments, the one or more glidant component comprises about 3% by weight of the pharmaceutical formulation. In some embodiments, the one or more glidant component comprises about 3% by weight of the pharmaceutical formulation. In some embodiments, the one or more glidant component comprises about 0.5% by weight of the pharmaceutical formulation.

In certain embodiments, the formulations of the present invention comprise one or more excipients selected from the group consisting of: the co-crystal, microcrystalline cellulose (e.g., Avicel PH113), lactose (e.g., Lactose-316 Fast Flo), croscarmellose sodium (e.g., Ac-Di-Sol), sodium lauryl sulfate, colloidal silica (e.g., fumed or amorphous silica; Cabosil M-5), sodium stearyl fumarate or a combination thereof.

In certain embodiments, the formulations of the present invention comprise the co-crystal, microcrystalline cellulose (e.g., Avicel PH113), lactose (e.g., Lactose Fast Flo), croscarmellose sodium (e.g., Ac-Di-Sol), sodium lauryl sulfate, colloidal silica (e.g., fumed or amorphous silica; Cabosil M-5), and sodium stearyl fumarate.

In certain embodiments, the formulations of the present invention comprise about 55 wt. % to 80 wt. % of the co-crystal, 8 wt. % to 13 wt. % of microcrystalline cellulose (e.g., Avicel PH113), 8 wt. % to 13 wt. % lactose (e.g., Lactose-316 Fast Flo), 1 wt. % to 7 wt. % of croscarmellose sodium (e.g., Ac-Di-Sol), 1 wt. % to 7 wt. % of sodium lauryl sulfate, 0.1 wt. % to 7 wt. % of colloidal silica (e.g., fumed or amorphous silica; Cabosil M-5), and 1 wt. % to 7 wt. % of sodium stearyl fumarate.

In certain embodiments, the formulations of the present invention comprise about 60 wt. % to 75 wt. % of the co-crystal, 10 wt. % to 12 wt. % of microcrystalline cellulose (e.g., Avicel PH113), 10 wt. % to 12 wt. % lactose (e.g., Lactose-316 Fast Flo), 1 wt. % to 5 wt. % of croscarmellose sodium (e.g., Ac-Di-Sol), 1 wt. % to 5 wt. % of sodium lauryl sulfate, 0.1 wt. % to 5 wt. % of colloidal silica (e.g., fumed or amorphous silica, Cabosil M-5), and 1 wt. % to 5 wt. % of sodium stearyl fumarate.

In certain embodiments, the formulations of the present invention comprise about 67 wt. % of the co-crystal, about 12 wt. % of microcrystalline cellulose (e.g., Avicel PH113), about 12 wt. % lactose (e.g., Lactose-316 Fast Flo), about 3 wt. % of croscarmellose sodium (e.g., Ac-Di-Sol), about 2 wt. % of sodium lauryl sulfate, about 1.0 wt. % of colloidal silica (e.g., fumed or amorphous silica, Cabosil M-5), and about 3 wt. % of sodium stearyl fumarate.

The pharmaceutical compositions of this invention may be orally administered in any orally acceptable dosage form including, but are not limited to, capsules, tablets, pills, powders, granules, aqueous suspensions or solutions. Other pharmaceutical compositions of the present invention (as well as compositions for use in methods, combinations, kits, and packs of the present invention) may be administered orally, parenterally, sublingually, by inhalation spray, topically, rectally, nasally, buccally, vaginally or via an implanted reservoir. The term "parenteral" as used herein includes subcutaneous, intravenous, intramuscular, intra articular, intra synovial, intrasternal, intrathecal, intrahepatic, intralesional and intracranial injection or infusion techniques. Preferably, the compositions are administered orally or intravenously.

Such administration can be used as a chronic or acute therapy. The amount of active ingredient that may be combined with the carrier materials to produce a single dosage form will vary depending upon the host treated and the particular mode of administration. The particular dose unit can be selected to accommodate the desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely.

The API and excipient(s) mixture can be prepared by, for instance, conventional mixing, compacting, granulating, compression, or coating. Procedures which may be used are known in the art, e.g., those described in L. Lachman et al. The Theory and Practice of Industrial Pharmacy, 3rd Ed, 1986, H. Sucker et al, Pharmazeutische Technologie, Thieme, 1991, Hagers Handbuch der pharmazeutischen Praxis, 4th Ed. (Springer Verlag, 1971) and Remington's Pharmaceutical Sciences, 13th Ed. (Mack Publ., Co., 1970) or later editions. Examples of such techniques are as follows:

(1) Blending of the API with the appropriate excipients using different blending equipment, such low shear blenders and high shear blenders;

(2) Direct compression of the blends, using appropriate punches and dies; the punches and dies are fitted to a suitable compaction machine, such as rotary tableting press or a single station compaction machine;

(3) The formulation blend can be granulated if necessary, using appropriate granulation methods such as dry granulation (slugging or roller compaction), high shear wet granulation, fluid bed granulation, extrusion-spheronization etc.;

(4) Granulation followed by compression; and (5) Coating of the tablets produced using appropriate coating equipment (e.g., coating pans) and appropriate coating solutions/suspensions to be applied on the tablets.

As indicated above, the formulations of the present invention find their greatest utility when administered to a subject who is in the fed or fasted state, preferably in the fed state.

The tablets may be produced by way of a conventional method or combinations of conventional methods such as roller compaction and direct compression method. For example, a tableting process is essential for production methods of tablets, and also the other processes such as of mixing, drying, and coating may be combined as required. The tableting process may be, for example, a direct compression method where the co-crystal and pharmaceutically acceptable excipients disclosed herein are mixed and then the mixture is compressed into tablets by use of tableting machines, or a wet granule-compression method or dry granule-compression method. The tableting machine for compression to produce tablets may be, for example, single-punch tableting machines, rotary tableting machines, or core-containing tableting machines.

In one embodiment of the invention, the tablet has a hardness in the range of about 4 to 20 kp (kilopond). The tablet of this embodiment may or may not comprise an outer coating as described below. In another embodiment, the tablet preferably has a hardness in the range of about 10 to 20 kp.

Yet in one embodiment of the present invention, the formulation includes tablet compositions that may be coated.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example #1

Preparation of VX-950 and 4-Hydroxybenzoic Acid Co-Crystal by Crystallization from Dichloromethane and Tert-Butyl Methyl Ether Solution Using a Co-Addition Process A slurry of VX-950/4-hydroxybenzoic acid co-crystal (3 wt %) in 3:5 dichloromethane to tert-butyl methyl ether (20 mL) was charged to a reactor with jacket temperature at 25° C. Solutions of VX-950 in dichloromethane (11.14 in 33.75 mL) and 4-hydroxybenzoic acid in tert-butyl methyl ether (2.5 g in 56.25 mL) were prepared in separate flasks. These solutions were then added via separate pumps to the reactor containing the co-crystal slurry at appropriate rates as to maintain a ratio of 1:1.1 VX-950 to 4-hydroxybenzoic acid and a solvent ratio of 3:5 dichloromethane to tert-butyl methyl ether. The addition time was approximately 10 hours. The slurry was stirred for approximately 10-12 hours before filtering. The filter cake was washed with 40 mL of 3:5 dichloromethane to tert-butyl methyl ether. The product was dried at 65° C. for 18-24 hours, which yielded 11.32 g of co-crystal with 99.4% AUC purity. This amount equates to an isolated yield of 82.3% taking into account the added seed. The epimer level was 0.51%. The residual solvent levels were 122 ppm for dichloromethane and 802 ppm for tert-butyl methyl ether. The molar ratio of VX-950 to 4-hydroxybenzoic acid was 1:0.96. The product consisted of rods up to 71 μm in length.

The co-addition process has been or could be performed with, but not limited to, the following permutations to the above-described steps:

Seed characteristics and parameters such as source, amount, pre-conditioning and processing could be altered for their effect on the bulk properties of the co-crystal.

The solvent composition for the solvents involved could be altered for its effect on yield, morphology and bulk properties of the co-crystal.

The temperature at which the crystallization takes place could be changed from 20-25° C.

The molar ratio of VX-950 to 4-hydroxybenzoic acid could be changed.

Time of addition for the two solutions could be altered for its effect on crystal growth.

Post-crystallization processing options while still in the slurry could include but are not limited to a) aging, b) controlled cooling, c) temperature cycles, d) wet milling or e) a combination thereof.

Washing the filtered wet cake with a solvent or solvent mixture is performed in some, but not all, cases.

Example #2

Preparation of VX-950 and 4-Hydroxybenzoic Acid Co-Crystal by Crystallization from Dichloromethane and Acetonitrile Solution Using a Co-Addition Process 1. Procedure A:

A slurry of VX-950/4-hydroxybenzoic acid co-crystal (3 wt. %) in 2:5 dichloromethane to acetonitrile (20 mL) was charged to a reactor with jacket temperature at 25° C. Solutions of VX-950 in dichloromethane (7 g in 28 mL) and 4-hydroxybenzoic acid in acetonitrile (1.79 g in 80 mL) were prepared in separate flasks. These solutions were then added via separate pumps to the reactor containing the co-crystal slurry at appropriate rates to maintain a ratio of 1:1.1 VX-950 to 4-hydroxybenzoic acid and a solvent ratio of 2:5 dichloromethane to acetonitrile. The addition time was approximately 10 hours. After the addition of the two solutions, the temperature of the reactor jacket was increased to 35° C. over 1 hour, and then decreased to 20° C. over two hours. Immediately following the first temperature cycle, the reactor jacket temperature was increased again to 35° C. over 1 hour and decreased to 20° C. over 6 hours. The slurry was stirred at 20° C. for 1 hour before filtering. The filter cake was washed with 14 mL of 2:5 dichloromethane to acetonitrile. The product was dried at 65° C. for approximately 18-24 hours.

2. Procedure B

A slurry of VX-950/4-hydroxybenzoic acid co-crystal (3.6 wt % based on VX-950 charge) in 2:5 dichloromethane to acetonitrile (4.29 L) was charged to a vessel with batch temperature ranging between 20-24° C. This initial slurry acted as a seed bed. Solutions of VX-950 (1500 g, 2.206 mol) in dichloromethane (6 L) and 4-hydroxybenzoic acid (335.2 g, 1.1 equivalents) in acetonitrile (15 L) were prepared in separate flasks. These solutions were then added via separate pumps to the vessel containing the co-crystal seed bed at appropriate rates to maintain a molar ratio of 1:1.1 VX-950 to 4-hydroxybenzoic acid and a solvent ratio of 2:5 dichloromethane to acetonitrile. The addition time was approximately 7 hours. The resulting slurry was stirred approximately 12 hours with the slurry temperature maintained at 22° C. The slurry then underwent temperature cycles. The temperature of the slurry was increased to 35° C. over 1 hour by increasing the jacket temperature of the vessel. The slurry was held at this temperature for 30 minutes and then was decreased over 2 hours to 22° C. by imposing a cooling ramp of 0.2° C./min on the jacket temperature. A second temperature cycle was performed in a similar manner with the exception that the cooling ramp to 20° C. took place over 6 hours. The slurry was maintained at 20° C. for 15 hours. The slurry was filtered and the filter cake was washed with 3.5 L of 2:5 dichloromethane to acetonitrile. The co-crystal was dried in vacuo at 70° C. for approximately 2-4 days, which yielded 1602 g of co-crystal with 99.49% AUC purity. This amount equates to an isolated yield of 86.2% taking into account the added seed. The epimer level was 0.51%. The residual solvent levels were 500 ppm for dichloromethane and <100 ppm for acetonitrile. The molar ratio of VX-950 to 4-hydroxybenzoic acid was 1:0.992. The product consisted predominantly of thick rods.

Example #3

Preparation of VX-950 and 4-Hydroxybenzoic Acid Co-Crystal by Crystallization from Dichloromethane and Ethyl Acetate Solution Using a Co-Addition Process 1. Procedure A:

A slurry of VX-950/4-hydroxybenzoic acid co-crystal (3 wt %) in 2:3 dichloromethane to ethyl acetate (20 mL) was charged to a reactor with jacket temperature at 25° C. Solutions of VX-950 in dichloromethane (9.00 g in 36 mL) and 4-hydroxybenzoic acid in ethyl acetate (2.01 g in 54.9 mL) were prepared in separate flasks. These solutions were then added via separate pumps to the reactor containing the co-crystal slurry at appropriate rates to maintain a ratio of 1:1.1 VX-950 to 4-hydroxybenzoic acid and a solvent ratio of 2:3 dichloromethane to ethyl acetate. The addition time was approximately 10 hours. After the addition of the two solutions, the temperature of the reactor jacket was increased to 35° C. over 1 hour, and then decreased to 20° C. over two hours. Immediately following the first temperature cycle, the reactor jacket temperature was increased again to 35° C. over 1 hour and decreased to 20° C. over 6 hours. The slurry was stirred at 20° C. for 1 hour before filtering. The filter cake was washed with 18 mL of 1:3 dichloromethane to ethyl acetate mixture. The product was dried at 65° C. for approximately 18-24 hours.

2. Procedure B:

A slurry of VX-950/4-hydroxybenzoic acid co-crystal (3.9 wt % based on VX-950 charge) in 2:3 dichloromethane to ethyl acetate (20 mL) was charged to a vessel with jacket temperature at 25° C. This initial slurry acted as a seed bed. Solutions of VX-950 (9.00 g, 13.2 mmol) in dichloromethane (36 mL) and 4-hydroxybenzoic acid (2.01 g, 1.1 equivalents) in ethyl acetate (54.9 mL) were prepared in separate flasks. These solutions were then added via separate pumps to the vessel containing the co-crystal seed bed at appropriate rates to maintain a ratio of 1:1.1 VX-950 to 4-hydroxybenzoic acid and a solvent ratio of 2:3 dichloromethane to ethyl acetate. The addition time was approximately 10 hours. After the addition of the two solutions was complete, the temperature of the reactor jacket was increased to 35° C. over 1 hour, and then decreased to 20° C. over two hours. A second cycle was performed in a similar manner with the exception that the cooling ramp to 20° C. took place over 6 hours. The slurry was stirred at 20° C. for 1 hour before filtering. The filter cake was washed with 18 mL of 1:3 dichloromethane to ethyl acetate. The co-crystal was dried in vacuo at 65° C. for approximately 18-24 hours, which yielded 9.38 g of co-crystal with 99.0% AUC purity. This amount equates to an isolated yield of 83.9% taking into account the added seed. The epimer level was 0.97%. The residual solvent levels were <100 ppm for dichloromethane and 263 ppm for ethyl acetate. The molar ratio of VX-950 to 4-hydroxybenzoic acid was 1:1.02. The product consisted predominantly of plates up to 32 μm in width and 75 μm in length.

Example #4

Preparation of VX-950 and 4-Hydroxybenzoic Acid Co-Crystal by Crystallization from Dichloromethane and Tert-Butyl Methyl Ether Solution Using an Anti-Solvent Addition Process 1. Procedure A:

A solution of VX-950 (200.2 g, 1 equivalent) and 4-hydroxybenzoic acid (44.8 g, 1.1 equivalents) in 13:7 dichloromethane to tert-butyl methyl ether (1.54 L) was prepared and charged to the reactor vessel with the jacket temperature at 22.5° C. Then, VX-950/4-hydroxybenzoic acid co-crystal (1.2 g, 0.5 wt %) was added as seed and allowed to stir for 1 hour during which the slurry thickened to give white solids. A pump was then started to deliver 1.13 L of tert-butyl methyl ether over 10 hours, yielding a final solvent ratio of 3:5 dichloromethane to tert-butyl methyl ether. The slurry was stirred for 4-5 hours before temperature cycles commenced. The temperature of the reactor jacket was increased to 35° C. over 1 hour, and then decreased to 20° C. over two hours. Immediately following the first temperature cycle, the reactor jacket temperature was increased again to 35° C. over 1 hour and decreased to 20° C. over 6 hours. The slurry was stirred for approximately 1 hour before filtering. The filter cake was washed with 500 mL of 3:5 dichloromethane to tert-butyl methyl ether. The product was dried at 65° C. for 36 hours.

2. Procedure B:

VX-950 (1500 g, 2.206 mol) and 16 L of a 13:7 mixture of dichloromethane to tert-butyl methyl ether were charged to a vessel with a jacket temperature set at 20° C. 4-hydroxybenzoic acid (457 g, 1.5 equivalents) was then charged to the vessel. The contents of the vessel were stirred for approximately 5 minutes until a solution resulted. Then, VX-950/4-hydroxybenzoic acid co-crystal (45 g, 3 wt % based on VX-950 charge) was added as seed. The slurry was stirred for 1 hour during which the co-crystal seed remained as a fine suspension. The anti-solvent, tert-butyl methyl ether (25.6 L) was then added via a pump over 6-7 hours, yielding a final solvent ratio of 1:3 dichloromethane to tert-butyl methyl ether. The slurry was stirred approximately 17 hours maintaining a temperature of about 20° C. The slurry was filtered and the resulting cake remained on the filter under vacuum with a nitrogen sweep for approximately 4.5 hours. No wash of the filter cake was performed. The co-crystal was dried in vacuo at about 60° C. for approximately 5 days. This process yielded 1693 g of co-crystal with 100% AUC purity. This amount equates to an isolated yield of 91.5% taking into account the added seed. Residual solvent levels were checked at this point and found to be high in comparison to other co-crystal lots prepared using the same procedure. Approximately 1374 g of co-crystal was submitted for further drying at approximately 70° C. After 3-4 additional days of drying, the residual solvents were 317 ppm for dichloromethane and 3876 ppm for tert-methyl butyl ether. The final dried co-crystal purity was 99.93% AUC. The epimer level was 0.07%. The molar ratio of VX-950 to 4-hydroxybenzoic acid was 1:1.001. The product consisted of thin rods.

This process of Procedure B has been or could be performed with, but not limited to, the following permutations to the above-described steps:

The temperature at which the crystallization takes place could be changed from 20-25° C.

The solvent composition at which seeding is performed could be altered.

The molar ratio of VX-950 to 4-hydroxybenzoic acid could be changed.

Seed characteristics and parameters such as source, amount, pre-conditioning, and processing could be altered for their effect on the bulk properties of the co-crystal.

Time of addition for the anti-solvent addition could be altered for its effect on crystal growth, batch processability, bulk properties of the co-crystal, etc. . . .

The final solvent composition for the solvents involved could be altered for its effect on yield, morphology and bulk properties of the co-crystal.

Post-crystallization processing options while still in the slurry could include but are not limited to a) aging, b) controlled cooling, c) temperature cycles, d) wet milling or e) a combination thereof.

Washing the filtered wet cake with a solvent or solvent mixture is performed in some, but not all, cases.

Example #5

Preparation of VX-950 and 4-Hydroxybenzoic Acid Co-Crystal by Crystallization from Dichloromethane and Acetone Solution VX-950 (1 g, 1.471 mmol) was charged into a reactor and then dissolved in dichloromethane (3.0 mL). In another flask, 4-hydroxybenzoic acid (264.1 mg, 1.912 mmol) was dissolved in acetone (3.0 mL). The solution of 4-hydroxybenzoic acid was added to the solution of VX-950 at ambient temperature. A thick suspension formed within 15 minutes. The suspension was filtered and the cake was washed with 10 mL of dichloromethane and acetone mixture (5 mL and 5 mL, respectively). The product was dried in vacuo at 60-70° C. for 35-40 hours. 0.35 g of product was obtained. This process has been or could be performed with, but not limited to, the following permutations to the above-described steps:

The temperature at which the crystallization takes place could be changed from 20-25° C.

The solvent composition for the solvents involved could be altered for its effect on yield, morphology and bulk properties of the co-crystal.

The molar ratio of VX-950 to 4-hydroxybenzoic acid could be changed.

In the example given above, the crystallization self-seeded such that the addition of co-crystal seed was not necessary. However, the crystallization batch can be seeded, if necessary. Seed characteristics and parameters such as source, amount, pre-conditioning, and processing could be altered for their effect on the bulk properties of the co-crystal.

Post-crystallization processing options while still in the slurry could include but are not limited to a) aging, b) controlled cooling, c) temperature cycles, d) wet milling or e) a combination thereof.

Washing the filtered wet cake with a solvent or solvent mixture is performed in some, but not all, cases.

Example 6

Preparation of VX-950 and 4-Hydroxybenzoic Acid Co-Crystal by Crystallization from Dichloromethane, Tetrahydrofuran and n-Heptane Solution Using an Anti-Solvent Addition Process VX-950 (10.1 g, 14.9 mmol) and 4-hydroxybenzoic acid (2.27 g, 1.1 equivalents) were charged to a vessel with the jacket temperature maintained at 22° C. A mixture of dichloromethane (45 mL) and tetrahydrofuran (15 mL) was then added to the vessel and the contents were stirred until the two components had dissolved. 18 mL of the anti-solvent, n-heptane, was then added via a syringe pump at a rate of 30 mL/hour. The contents of the vessel remained in solution. VX-950/4-hydroxybenzoic acid co-crystal (300 mg, 3 wt % based on VX-950 charge) was then added as seed. The slurry was stirred for 45-60 minutes during which the co-crystal seed remained as a fine suspension. Addition of next 8.1 mL of n-heptane continued at a rate of approximately 4 mL/hour. The remaining n-heptane (50.26 mL) was added at a rate of 8.1 mL/hour. After the addition of n-heptane was complete, the slurry was stirred for 16-22 hours maintaining the vessel jacket temperature at 22° C. The slurry was filtered. No wash of the filter cake was performed. The co-crystal was dried in vacuo at 60-65° C. for approximately 35-48 hours. This process yielded 11.53 g of co-crystal with 99.97% AUC purity. This amount equates to an isolated yield of 92.6% taking into account the added seed. The residual solvent levels were 354 ppm for dichloromethane, 457 ppm for tetrahydrofuran and 123 ppm for n-heptane. The molar ratio of VX-950 to 4-hydroxybenzoic acid was 1:1.008. The product consisted predominantly of thin rods.

This process has been or could be performed with the following permutations:

The temperature at which the crystallization takes place could be changed from 20-25° C.

The solvent composition at which seeding is performed could be altered.

The molar ratio of VX-950 to 4-hydroxybenzoic acid could be changed.

Seed characteristics and parameters such as source, amount, pre-conditioning, and processing could be altered for their effect on the bulk properties of the co-crystal.

Time of addition for the anti-solvent addition could be altered for its effect on crystal growth, batch processability, bulk properties of the co-crystal, etc. . . .

The final solvent composition for the solvents involved could be altered for its effect on yield, morphology and bulk properties of the co-crystal.

Post-crystallization processing options while still in the slurry could include but are not limited to a) aging, b) controlled cooling, c) temperature cycles, d) wet milling or e) a combination thereof.

Washing the filtered wet cake with a solvent or solvent mixture is performed in some, but not all, cases.

Example 7

Preparation of VX-950 and 4-Hydroxybenzoic Acid Co-Crystal in which Particle Size Control is Effected During the Crystallization VX-950 and 4-hydroxybenzoic acid co-crystal was prepared at a 30 g scale using a procedure similar to that described in example #4 with the exception that 20 wt % (based on the initial VX-950 amount) of jet-milled seed was charged. This process yielded 36.98 g of co-crystal with 100% AUC purity. This amount equates to an isolated yield of 87.6% taking into account the added seed. The resulting co-crystal contained residual solvent levels of <100 ppm for dichloromethane and 446 ppm for tert-butyl methyl ether. The molar ratio of VX-950 to 4-hydroxybenzoic acid was 1:1.01. In contrast to other batches, the resulting co-crystal consisted of small particles rather than thin rods. Particle size control could also be achieved by altering one or more process parameters (e.g. solvent type, time of addition, seed amount, seed point, etc. . . . ).

Example 8

X-Ray Powder Diffraction and Differential Scanning Calorimetry of the VX-950 Co-Crystal The VX-950/HBA co-crystal has at least two of the five X-ray powder diffraction peaks at about 7.684, 8.599, 9.605, 9.938, 12.872°2-Theta, each with a standard deviation of about +/−0.3° 2-Theta. In some embodiments, the co-crystal has a DSC peak in its DSC thermogram with a peak onset at about 188.67° C. with a standard deviation of about +/−5° C.

Example 9

Comparison of the Kinetic Solubility of a Co-Crystal that Includes VX-950 and 4-Hydroxybenzoic Acid with that of Crystalline VX-950 in 1% SLS Aqueous Media As shown in FIG. 1, the kinetic solubility of an example of a co-crystal disclosed herein is significantly higher than that of crystalline VX-950 in 1% SLS, as well as in simulated gastric and intestinal fluids. Thus, the co-crystal may provide enhanced VX-950 absorption in vivo compared to crystalline VX-950.

Example 10

Preparation of Immediate Release Tablets Containing VX-950:4-Hydroxybenzoic Acid Co-Crystal, In Vitro Dissolution and In Vivo Exposures from Immediate Release Formulations of VX-950 Co-Crystal Table 1 shows an example of the formulations disclosed herein in a tablet form.

TABLE 1

Composition of VX-950: 4-HBA co-crystal tablets

| Components | Grade | % wt of Tablet |
|---|---|---|
| VX-950 co-crystal | N/A | 67.8 |
| Microcrystalline Cellulose | Avicel PH1113 | 11.71 |
| Lactose | Fast-Flo #316 | 11.71 |
| Sodium Lauryl Sulfate (SLS) | [NF Grade] | 2 |
| Croscarmellose Sodium | AcDiSol | 3 |
| Sodium Stearyl Fumarate | N/A | 3 |
| Collodial Silica | Cabosil M-5 | 0.78 |

One possible process used for making the tablets involved the following steps:

The active ingredient (the co-crystal that includes VX-950) was processed to reduce particle size by an appropriate milling method (e.g., sieving, fitz-milling, comilling, jet-milling, crushing etc.). In one particular example, a comill was used to delump the co-crystal API. In one particular example, the co-crystal was passed through a 40 G screen at 1000 rpm.

The active ingredient was blended with the appropriate excipients, apart from the lubricant, using appropriate blending methods (e.g., v-shell blender). In one particular example, the active ingredient was blended with the appropriate excipients using a V-shell blender at 32 rpm for 6 min.

The formulation blend can be granulated if necessary. In some examples dry granulation via roller compaction was used, and in other examples the formulation blend was directly compressed (after lubrication). In one particular example, the blend was roller compacted using a Vector TF-mini roller compactor at 650 psi.

The formulation granules were lubricated by blending with lubricant in an appropriate blender. In one particular example, the roller compacted ribbons were milled using a Quadro comil using a 40 G screen at 1000 rpm.

In one particular example, the granules were lubricated using a V-shell blender at 32 rpm for 6 min The lubricated granules were compressed into tablets using an appropriate compression machine (tablet press). In one particular example, the lubricated formulation was compressed into tablets using a Piccola rotary tablet press, targeting 1000 mg tablet weight and a tablet hardness range of 14-17 kp.

Figure 2:
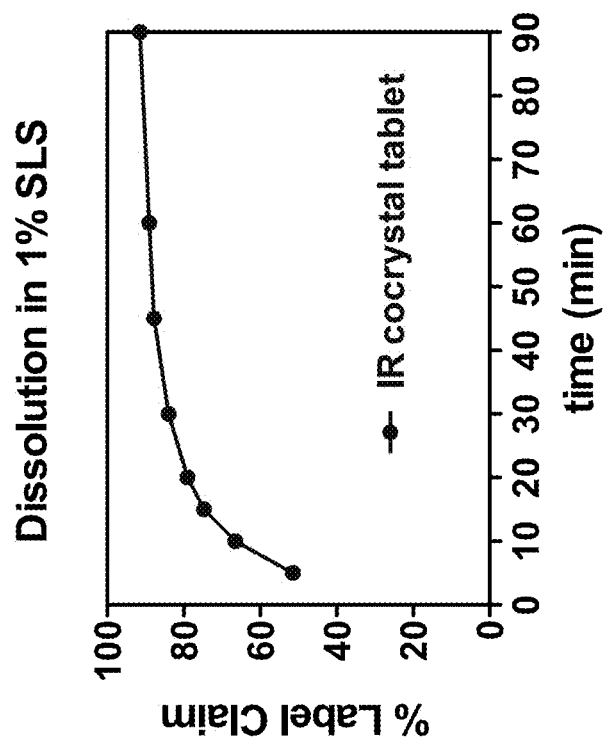
FIGS. 2 and 3 show dissolution data of immediate release formulations that have the VX-950:4-hydroxybenzoic acid co-crystal in 1% sodium lauryl sulfate (SLS) media and Fed Simulated Gastric Fluid (FeSSGF) media.
Figure 3:
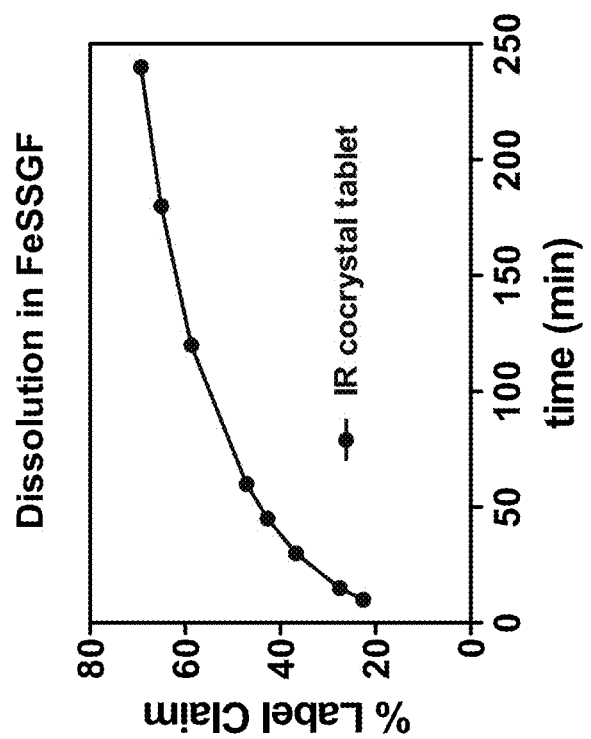

FIGS. 2 and 3 demonstrate dissolution data of immediate release VX-950 co-crystal tablet formulations of the present invention in 1% SLS and in FeSSGF. Good dissolution is observed by the immediate release co-crystal tablets in vitro, even in FeSSGF despite the solubility limitations.

The co-crystal tablets of the present invention have also been dosed to male beagle dogs to verify good exposure from the various tablet formulations. The dogs were dosed in the fed state. The animals were acclimated to a feeding schedule for seven (7) days prior to dosing; animals were fasted overnight, then provided with a measured quantity of food at a particular time. The day of the dosing the animals were fed, pre-dose blood samples were obtained and then the test article was administered via oral gavage to animals. Blood collection was performed at 15 and 30 minutes, 1, 2, 3, 4, 6, 8, 12, and 24 hours following dosing to obtain pharmacokinetic parameter information.

The results from a representative formulation described above in Table 1 are summarized in Table 2.

TABLE 2

Dose normalized AUC (µg*hr/mL/mg), $T_{max}$ and % F after dosing VX-950: 4-HBA immediate release cocrystal tablets to fed male beagle dogs (dose: 562.5 mg of VX-950)

| Formulation | Dose Normalized $AUC_{inf}$ (µg*hr/mL/mg) | $T_{max}$ (hr) | % F |
|---|---|---|---|
| Immediate Release Tablet[1] | 0.033 ± 0.017 | 1.84 ± 1.26 | 29.62 ± 16.52 |

[1]An example of this table is described in Table 1.

Example 11

In-Vitro Apparent Solubility of VX-950:4-HBA Co-Crystal and Formulation

Apparent solubility values of representative VX-950:4-HBA co-crystal drug substance and formulation materials are being reported based the average number of samples tested under kinetic solubility conditions. The testing condition is to dispense an amount of powder into a dissolution medium.

Analysis is conducted to determine the cumulative amount of VX-950 detected in the medium with respect to time and reported as mgs VX-950 per mL of medium. It should be noted that the data below is a representative set to show that the VX-950:4-HBA co-crystal and formulation dissolves in certain amounts in the recited media.

In simulated fed state intestinal fluid (FeSSIF) VX-950:4-HBA co-crystal drug substance was tested using two lots of drug substance with three replicates per lot (total N=6) at a concentration relative to VX-950 of 0.62 mg/mL. An immediate release roller-compacted granule formulation of VX-950:4-HBA co-crystal ("VX-950;4-HBA Co-crystal IR/RC granules"; e.g., the ingredients of the formulation described in Table 1) were tested in duplicate (N=2) using a single lot at a concentration relative to VX-950 of 0.63 mg/mL. The apparent solubility data in FeSSIF is presented in Table 3.

TABLE 3

Apparent solubility of VX-950: 4-HBA co-crystal and formulation in fed state simulated intestinal fluid (FeSSIF)

| Material in FeSSIF | Apparent solubility in mg/mL (Test time-1 hour) | Apparent Maximum solubility in mg/mL (Test time-hours) |
|---|---|---|
| VX-950; 4-HBA Co-crystal | 0.133 (t = 1 hr) | 0.146 (t = 1.5 hrs) |
| VX-950; 4-HBA Co-crystal IR/RC granules | 0.122 (t = 1 hr) | 0.126 (t = 3 hrs) |

For experiments in simulated fed state gastric fluid (FeSSGF) dissolution medium, the VX-950:4-HBA co-crystal drug substance was tested using two lots of drug substance with three replicates per lot (total N=6) at a concentration relative to VX-950 of 0.91 mg/mL, The apparent solubility data in FeSSGF is presented in Table 4.

TABLE 4

Apparent solubility of VX-950: 4-HBA co-crystal and formulation in fed state simulated gastric fluid (FeSSGF)

| Material in FeSSGF | Apparent solubility in mg/mL (Test time-1 hour) | Apparent Maximum solubility in mg/mL (Test time-hours) |
|---|---|---|
| VX-950; 4-HBA Co-crystal | 0.488 (t = 1 hr) | 0.645 (t = 5 hr) |

Kinetic solubility experiments in 1% SLS dissolution medium were conducted under sink conditions at a concentration relative to VX-950 of 0.63 mg/mL. The VX-950:4-HBA co-crystal drug substance was tested using four lots of drug substance (total N=10 replicates). The VX-950;4-HBA Co-crystal IR/RC granules were tested in duplicate (N=2) using a single lot at a concentration relative to VX-950 of 0.63 mg/mL. The apparent solubility data in 1% SLS is presented in Table 5.

TABLE 5

Apparent solubility of VX-950: 4-HBA co-crystal and formulation in 1% Sodium Lauryl Sulfate (SLS) dissolution medium

| Material in 1% SLS | Apparent solubility in mg/mL (Test time-1 hour) | Apparent Maximum solubility in mg/mL (Test time-hours) |
|---|---|---|
| VX-950; 4-HBA Co-crystal | 0.589 (t = 1 hr) | 0.597 (t = 3 hr)[a] |
| VX-950; 4-HBA Co-crystal IR/RC granules | 0.593 (t = 1 hr) | 0.602 (t = 3 hr) |

[a]This value is taken as the average of N = 5 as not all lots were tested to this time point All publications and patents cited in this specification are herein incorporated by reference as if each individual publication or patent were specifically and individually indicated to be incorporated by reference. Although the foregoing invention has been described in some detail by way of illustration and example for purposes of clarity or understanding, it will be readily apparent to those of ordinary skill in the art in light of the teachings of this invention that certain changes and modifications may be made thereto without departing from the spirit or scope of the appended claims.

We claim:

1. A pharmaceutical composition comprising:
an active ingredient, and
one or more excipients present in an amount about at least 1% of the total weight of the formulation, wherein
the active ingredient comprises a co-crystal, the co-crystal comprising VX-950 and a co-former of 4-hydroxybenzoic acid,
wherein the co-crystal is present in amount about at least 68% of the total weight of the formulation.

2. The formulation of claim 1, wherein the molar ratio of the active ingredient with respect to the co-former ranges from about 5:1 to about 1:5.

3. The formulation of claim 2, wherein the molar ratio of VX-950 with respect to the co-former is about 1:1.

4. The formulation of claim 1, wherein the one or more excipients is selected from the group consisting of a filler, a surfactant, a glidant, a lubricant and a disintegrant.

5. The formulation of claim 1, wherein the one or more excipients comprises one or more fillers.

6. The formulation of claim 5, wherein the one or more fillers is selected from one or more from the group consisting of the following: mannitol, lactose, sucrose, dextrose, maltodextrin, sorbitol, xylitol, powdered cellulose, microcrystalline cellulose, silicified microcrystalline cellulose, methylcellulose, ethylcellulose, hydroxyethylcellulose, methylhydroxyethylcellulose, talc, starch, pregelatinized starch, dibasic calcium phosphate, calcium sulfate and calcium carbonate.

7. The formulation of claim 6, wherein the one or more fillers is microcrystalline cellulose, lactose or a combination thereof.

8. The formulation of claim 6, wherein the one or more fillers are microcrystalline cellulose, and lactose.

9. The formulation of claim 1, wherein the one or more excipients comprises one or more disintegrants.

10. The formulation of claim 9, wherein the one or more disintegrants is selected from one or more from the group consisting of the following: croscarmellose sodium, sodium alginate, calcium alginate, alginic acid, starch, pregelatinized starch, sodium starch glycolate, crospovidone, cellulose and its derivatives, carboxymethylcellulose calcium, carboxymethylcellulose sodium, soy polysaccharide, guar gum, an ion exchange resin, an effervescent system based on food acids and an alkaline carbonate component, and sodium bicarbonate.

11. The formulation of claim 10, wherein the one or more disintegrants is croscarmellose sodium.

12. The formulation of claim 1, wherein the one or more excipients comprises one or more surfactants.

13. The formulation of claim 1, wherein the one or more surfactants is selected from one or more from the group consisting of the following: sodium lauryl sulfate, docusate sodium, polyoxyethylene sorbitan fatty acid esters, polyoxyethylene 20 stearyl ethers, polyoxyethylene alkyl ethers, polyoxyethylene castor oil derivatives, pegylated hydrogenated castor oils, sorbitan esters of fatty acids, Vitamin E or tocol derivatives, vitamin E TPGS, tocopheryl esters, lecithin, phospholipids and their derivatives, poloxamers, stearic acid, oleic acid, oleic alcohol, cetyl alcohol, mono and diglycerides, propylene glycol esters of fatty acids, glycerol esters of fatty acids, ethylene glycol palmitostearate, polyoxylglycerides, propylene glycol monocaprylate, propylene glycol monolaurate and polyglyceryl oleate.

14. The formulation of claim 13, wherein the one or more surfactants is sodium lauryl sulfate.

15. The formulation of claim 1, wherein the one or more excipients includes one or more glidants.

16. The formulation of claim 15, wherein the one or more glidants is selected from one or more from the group consisting of the following: talc, colloidal silica, magnesium oxide, magnesium silicate, leucine and starch.

17. The formulation of claim 16, wherein the one or more glidants is colloidal silica.

18. The formulation of claim 1, wherein the one or more excipients includes one or more lubricants.

19. The formulation of claim 18, wherein the one or more lubricants is selected from one or more from the group consisting of the following: talc, fatty acid, stearic acid, magnesium stearate, calcium stearate, sodium stearate, glyceryl monostearate, sodium lauryl sulfate, sodium stearyl fumarate, hydrogenated oils, fatty alcohol, fatty acid ester, glyceryl behenate, mineral oil, vegetable oil, leucine, sodium benzoate, or a combination thereof.

20. The formulation of claim 19, wherein the one or more lubricants is sodium stearyl fumarate.

21. The formulation of claim 1 comprising:
about 68 wt. % of the co-crystal,
about 12 wt. % of a first filler;
about 12 wt. % of a second filler;
about 3 wt. % of a disintegrant;
about 2 wt. % of a surfactant;
about 1 wt. % of a glidant; and
about 3 wt. % of a lubricant.

22. The formulation of claim 1, wherein the one or more excipients comprises microcrystalline cellulose, lactose, croscarmellose sodium, sodium lauryl sulfate, colloidal silica and sodium stearyl fumarate.

23. The formulation of claim 1 comprising:
about 68 wt. % of the co-crystal,
about 12 wt. % of microcrystalline sodium;
about 12 wt. % lactose;
about 3 wt. % of croscarmellose sodium;
about 2 wt. % of sodium lauryl sulfate;
about 1 wt. % of colloidal silica; and
about 3 wt. % of sodium stearyl fumarate.

24. The formulation of claim 1, wherein the formulation is in a form of a capsule, tablet, pill, powder, granule, aqueous suspension or solution.

25. The formulation of claim 24, wherein the formulation is in a form of a capsule.

26. The formulation of claim 24, wherein the formulation is in a form of a tablet.

27. The formulation of claim 26, wherein the tablet is coated.

28. The formulation of claim 1, wherein the formulation is an immediate release formulation.

* * * * *